US012773209B1

(12) United States Patent
Holdmeyer et al.

(10) Patent No.: US 12,773,209 B1
(45) Date of Patent: Oct. 27, 2026

(54) MECHANICAL INFRASTRUCTURE TO SUPPORT ELECTRONICS IN AN END EFFECTOR OF A SURGICAL STAPLING INSTRUMENT

(71) Applicant: Cilag GmbH International, Zug (CH)

(72) Inventors: Seth Holdmeyer, Cincinnati, OH (US); Adam Hensel, Gahanna, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/212,572

(22) Filed: May 19, 2025

(51) Int. Cl.
*A61B 17/072* (2006.01)
*A61B 17/00* (2006.01)
*A61B 34/30* (2016.01)

(52) U.S. Cl.
CPC .................. *A61B 17/07207* (2013.01); *A61B 2017/00398* (2013.01); *A61B 2017/07257* (2013.01); *A61B 2017/07271* (2013.01); *A61B 2017/07278* (2013.01); *A61B 2017/07285* (2013.01); *A61B 34/30* (2016.02)

(58) Field of Classification Search
USPC ...................................................... 227/180.1
See application file for complete search history.

(56) References Cited

U.S. PATENT DOCUMENTS

| | | | |
|---|---|---|---|
| 5,395,033 A | 3/1995 | Byrne et al. | |
| 7,644,848 B2 | 1/2010 | Swayze et al. | |
| 7,721,931 B2 | 5/2010 | Shelton, IV et al. | |
| 8,753,338 B2 | 6/2014 | Widenhouse et al. | |
| 9,265,585 B2 | 2/2016 | Wingardner et al. | |
| 9,615,888 B2 | 4/2017 | Manzo et al. | |
| 9,668,735 B2 | 6/2017 | Beetel | |
| 9,877,718 B2 | 1/2018 | Weir et al. | |
| 10,190,888 B2 | 1/2019 | Hryb et al. | |
| 10,206,678 B2 | 2/2019 | Shelton, IV et al. | |
| 10,271,844 B2 | 4/2019 | Valentine et al. | |
| 10,595,836 B2 | 3/2020 | Smaby et al. | |
| 10,828,030 B2 | 11/2020 | Weir et al. | |
| 11,559,366 B2 | 1/2023 | Overmyer et al. | |
| 11,653,915 B2 | 5/2023 | Shelton, IV et al. | |
| 11,931,026 B2 * | 3/2024 | Wise | A61B 34/30 |
| 11,937,816 B2 | 3/2024 | Huang | |
| 11,992,210 B2 | 5/2024 | Shelton, IV et al. | |

(Continued)

FOREIGN PATENT DOCUMENTS

| | | |
|---|---|---|
| EP | 0679367 A2 | 11/1995 |
| EP | 2364666 A1 | 9/2011 |
| WO | 2012112249 A1 | 8/2012 |

*Primary Examiner* — Chinyere J Rushing-Tucker
(74) *Attorney, Agent, or Firm* — Barnes & Thornburg LLP

(57) ABSTRACT

A surgical instrument includes an end effector having an elongated jaw with a pair of side walls separated by a floor, which define a channel. Each of the side walls has an inner surface that defines a groove, and the groove defined by each side wall is in communication with the channel. A surgical staple reload cartridge may be received in the channel. The cartridge includes a top rail on either side and one or more bottom pads on either side, which also define grooves on either side of the cartridge. When positioned in the channel, the top rails and the bottom pads engage in inner surface of the respective side walls, and the grooves defined in the side walls of the end effector are in communication with respective grooves defined in the sides of the cartridges. Other embodiments are described and claimed.

20 Claims, 18 Drawing Sheets

(56) References Cited

U.S. PATENT DOCUMENTS

| | | | |
|---|---|---|---|
| 12,082,806 | B2 | 9/2024 | Giordano et al. |
| 12,268,388 | B2 | 4/2025 | Fiebig et al. |
| 12,484,900 | B2 | 12/2025 | Ryle et al. |
| 12,544,067 | B2 | 2/2026 | Batty et al. |
| 2006/0025810 | A1* | 2/2006 | Shelton, IV ..... A61B 17/07207 606/205 |
| 2011/0163147 | A1* | 7/2011 | Laurent ................ A61B 17/072 227/175.1 |
| 2016/0030042 | A1 | 2/2016 | Heinrich et al. |
| 2018/0042658 | A1 | 2/2018 | Shelton, IV et al. |
| 2019/0015102 | A1 | 1/2019 | Baber et al. |
| 2019/0200997 | A1 | 7/2019 | Shelton, IV et al. |
| 2024/0366221 | A1 | 11/2024 | Marriott et al. |
| 2024/0415510 | A1 | 12/2024 | Schings et al. |
| 2024/0423615 | A1 | 12/2024 | Shelton, IV et al. |
| 2025/0000510 | A1 | 1/2025 | Creamer et al. |
| 2025/0017585 | A1 | 1/2025 | Nalagatla et al. |
| 2025/0025155 | A1 | 1/2025 | Batty et al. |
| 2025/0025156 | A1 | 1/2025 | Shelton, IV et al. |
| 2025/0025157 | A1 | 1/2025 | Batty et al. |
| 2025/0025158 | A1 | 1/2025 | Ryle et al. |
| 2025/0025159 | A1 | 1/2025 | Batty et al. |
| 2025/0025160 | A1 | 1/2025 | Batty et al. |
| 2025/0025162 | A1 | 1/2025 | Ahrens et al. |
| 2025/0025164 | A1 | 1/2025 | Batty et al. |
| 2025/0025165 | A1 | 1/2025 | Ryle et al. |
| 2025/0025167 | A1 | 1/2025 | Ryle et al. |
| 2025/0025168 | A1 | 1/2025 | Ryle et al. |
| 2025/0025169 | A1 | 1/2025 | Batty et al. |
| 2025/0025170 | A1 | 1/2025 | Bertram et al. |
| 2025/0120718 | A1 | 4/2025 | Shelton, IV et al. |
| 2025/0312040 | A1 | 10/2025 | Overmyer |
| 2025/0375200 | A1 | 12/2025 | Batty et al. |

* cited by examiner

MECHANICAL INFRASTRUCTURE TO SUPPORT ELECTRONICS IN AN END EFFECTOR OF A SURGICAL STAPLING INSTRUMENT

TECHNICAL FIELD

The present disclosure relates generally to surgical instruments and, more particularly, to surgical stapling and cutting instruments and associated staple cartridges for use with the surgical instruments to facilitate the cutting and stapling of patient tissue.

BACKGROUND

Surgical procedures often involve the use of various surgical instruments to assist a surgeon in the performance of the corresponding procedure. Recently, minimally invasive surgical (MIS) instruments have gained preference over traditional "open" surgical devices as the use of MIS instruments can reduce post-operative recovery time and associated tissue scarring. Endoscopy and laparoscopy are common types of MIS procedures in which a tube or trocar is inserted into natural or surgically-made openings (e.g., incisions) of the patient, depending on the particular procedure. The tube or trocar is then used to facilitate introduction of associated surgical instruments into the patient's body (e.g., the patient's abdominal cavity) to treat internal tissue of the patient.

One type of surgical instrument usable in MIS procedures is a surgical stapler, sometimes referred to as an "endocutter." A typical surgical stapler includes an elongated shaft to facilitate use of a trocar and an end effector located at a distal end of the elongated shaft. The elongated shaft facilitates the use of the surgical stapler with a trocar to access the patient's anatomical environment (e.g., the patient's abdominal cavity) and may include one or more articulation joints to increase the usability of the surgical stapler in the anatomical environment. Similarly, the end effector may be attached to the elongated shaft via an articulation joint to allow the end effector to be positioned as desired by the surgeon. A typical end effector of a surgical stapler includes a pair of jaws movable between an open position and a closed position to facilitate the grasping of tissue within the jaws. One of the jaws is embodied as a cartridge jaw and is configured to receive a staple cartridge, and the other jaw is embodied as an anvil jaw configured to provide a surface on which the staples are formed. The end effector also includes a cutting element (typically referred to as a "knife"), which is translated distally along the end effector during a firing phase of the surgical stapler to transect tissue presently grasped by the end effector. As the knife advances along the end effector, staples contained in the staple cartridge are progressively ejected to thereby seal opposing sides of the transected tissue.

Surgical staplers may be embodied as independent, hand-held devices or configured to be coupled to a robotic surgery system. In hand-held embodiments, the surgical stapler may include a handle and an associated trigger, which is operable by a surgeon to control the end effector and the ejection of the staples from the staple cartridge. In robotic embodiments, the surgical stapler is configured to be mounted to a robotic arm of a robotic manipulator, which is controllable by the surgeon via a remote control console. For example, the control console may include various input devices that can be grasped and manipulated by the surgeon to cause movement and firing of the surgical stapler.

SUMMARY

According to one aspect, a surgical instrument includes an end effector. The end effector includes an elongated jaw that extends to a distal end. The jaw includes a first side wall, a second side wall, and a floor coupled between the first side wall and the second side wall, wherein the first side wall, the second side wall, and the floor cooperate to define a channel extending to the distal end. The first side wall includes an inner surface extending upward from the floor. The inner surface includes a footer, a first ledge extending outwardly from the footer, a groove surface extending upward from the first ledge, a second ledge extending inwardly from the groove surface, and a header extending upward from the second ledge. The first ledge, the groove surface, and the second ledge cooperate to define a groove in the first side wall, wherein the groove is in communication with the channel.

In an embodiment, the end effector further includes an I-beam comprising a knife that is moveable along the elongated jaw to the distal end. The surgical instrument further includes an elongated shaft that extends from a distal end to a proximal end, wherein the distal end of the elongated shaft is coupled to the end effector, and wherein the elongated shaft comprises a drivetrain coupled to the I-beam of the end effector.

In an embodiment, the surgical instrument further includes a handpiece coupled to the proximal end of the elongated shaft. The handpiece is configured to drive the drivetrain. In an embodiment, the surgical instrument further includes comprising a robotic tool interface coupled to the proximal end of the elongated shaft. The robotic tool interface is configured to drive the drivetrain.

In an embodiment, the floor of the elongated jaw further comprises a first slot wall extending downward from the floor and a second slot wall facing the first slot wall and extending downward from the floor in parallel, a first curved slot wall and a second curved slot wall extending outward from the first slot wall and the second slot wall, respectively, in opposing directions, and a slot floor connecting the first curved slot wall and the second curved slot wall. The first slot wall, the second slot wall, the first curved slot wall, the second curved slot wall, and the slot floor cooperate to define an elongated slot that extends to the distal end. The slot is in communication with the channel. In an embodiment, the first curved slot wall further includes a first inner cutout wall that extends outward to a first curved end wall, the second curved slot wall further includes a second inner cutout wall that extends outward, in an opposing direction to the first inner cutout wall, to a second curved end wall. The first inner cutout wall and the first curved end wall cooperate to define a first slot side annex, and the second inner cutout wall and the second curved end wall cooperate to define of a second slot side annex.

In an embodiment, the end effector further includes an I-beam comprising a knife and a lower beam, wherein the lower beam is received in the slot. In an embodiment, the surgical instrument further includes an elongated shaft that extends from a distal end to a proximal end. The distal end is coupled to the end effector, and the elongated shaft includes a drivetrain coupled to the I-beam. In an embodiment, the surgical instrument further includes a handpiece coupled to the proximal end of the elongated shaft, wherein the handpiece is configured to drive the drivetrain. In an embodiment, the surgical instrument further includes a robotic tool interface coupled to the proximal end of the elongated shaft, wherein the handpiece is configured to drive the drivetrain.

In an embodiment, the jaw extends from a hinge to the distal end, and the end effector further includes an elongated anvil extending from a proximal end to a distal end. The proximal end is hingedly coupled to the hinge of the jaw. The anvil is rotatable about the hinge from an open position in which the distal end of the anvil is spaced apart from the distal end of the jaw to a closed position in which the distal end of the anvil is close to the distal end of the jaw.

In an embodiment, the surgical instrument further includes an elongated staple cartridge positioned in the channel of the jaw. The staple cartridge includes an elongated body extending from a proximal end to a distal nose. The elongated body includes a first side wall extending from the proximal end to the distal nose. The first side wall includes a top rail extending outward from a top edge of the first side wall and extending from the proximal end to the distal nose. The first side wall includes a first bottom rail extending outward from a bottom edge of the first side wall, and a first bottom pad extending outward from the first bottom rail. The first side wall, the top rail, and the first bottom rail cooperate to define a side groove. An outer surface of the top rail of the staple cartridge engages the header of the first side wall, an outer surface of the first bottom pad engages the footer of the first side wall, and a bottom surface of the first side wall engages the floor of the jaw. The side groove defined in the staple cartridge is in communication with the groove defined in the first side wall. In an embodiment, the first bottom pad is positioned at an intermediate position between the proximal end and the distal nose. In an embodiment, the surgical instrument further includes a second bottom pad extending outward from the bottom edge of the first side wall, wherein the second bottom pad is positioned at a second intermediate position between the proximal end and the distal nose. In an embodiment, the first bottom pad extends from the proximal end to the distal nose.

In an embodiment, the elongated body of the staple cartridge further includes a deck extending from the proximal end to the distal nose. The deck is coupled to the first side wall at the top rail. The elongated body of the staple cartridge further includes a first inner wall extending downward from the deck, and extending parallel to the first side wall from the proximal end to a first position proximal of the distal nose. A central slot is defined through the deck by the first inner wall from the proximal end to the first position. A plurality of staple openings are defined in the deck. An elongated bottom opening opposite the plurality of staple openings is defined between the first side wall and the first inner wall. In an embodiment, the staple cartridge further includes a first side column coupled to the first side wall and extending from the deck to the bottom opening, wherein a bottom surface of the first side column engages the floor of the jaw, a second side column coupled to the first inner wall and extending from the deck to the bottom opening, and a first inner column extending from the deck to the bottom opening. The first side column, the second side column, and the first inner column cooperate to define a first driver channel from the bottom opening to one or more staple openings of the plurality of staple openings. In an embodiment, the surgical instrument further includes a first surgical staple positioned in the first driver channel, and a first driver positioned in the first driver channel. The first driver has a top saddle configured to engage the first surgical staple, wherein the first surgical staple is positioned between the first driver and the deck. When the first driver is moved within the first driver channel from a first position that is closer to the bottom opening to a second position that is closer to the one or more staple openings, the first driver ejects the first surgical staple out of the one or more staple openings.

In an embodiment, the surgical instrument further includes a second surgical staple and a third surgical staple positioned in the first driver channel. The first driver further includes a second top saddle configured to engage the second surgical staple and a third top saddle configured to engage the third surgical staple. When the first driver is moved within the first driver channel from the first position to the second position, the first driver ejects the second surgical staple and the third surgical staple out of the one or more staple openings.

In an embodiment, the staple cartridge further includes a sled coupled to the elongated body. The sled has a central fin that extends upward into the central slot and a first angled fin that extends upward through the bottom opening. The sled is moveable from a proximal position to a distal position. When the sled is moved from the proximal position to the distal position, the first angled fin engages an angled bottom surface of the first driver and causes the first driver to move from the first position to the second position.

According to another aspect, a staple cartridge for a surgical instrument includes an elongated body extending from a proximal end to a distal nose. The elongated body includes a first side wall extending from the proximal end to the distal nose. The first side wall includes a top rail extending outward from a top edge of the first side wall and extending from the proximal end to the distal nose. The first side wall includes a first bottom pad extending outward from a bottom edge of the first side wall. The first side wall, the top rail, and the first bottom pad cooperate to define a side groove.

In an embodiment, the top rail includes a flat outer surface, the bottom pad includes a flat outer surface, and the first side wall includes a bottom surface. In an embodiment, the first bottom pad is positioned at an intermediate position between the proximal end and the distal nose. In an embodiment, the staple cartridge further includes a second bottom pad extending outward from the bottom edge of the first side wall. The second bottom pad is positioned at a second intermediate position between the proximal end and the distal nose. In an embodiment, the first bottom pad extends from the proximal end to the distal nose.

In an embodiment, the elongated body further includes a deck extending from the proximal end to the distal nose. The deck is coupled to the first side wall at the top rail. The elongated body further includes a first inner wall extending downward from the deck, and extending parallel to the first side wall from the proximal end to a first position proximal of the distal nose. A central slot is defined through the deck by the first inner wall from the proximal end to the first position. A plurality of staple openings are defined in the deck. An elongated bottom opening opposite the plurality of staple openings is defined between the first side wall and the first inner wall.

In an embodiment, the elongated body further includes a first side column coupled to the first side wall and extending from the deck to the bottom opening, a second side column coupled to the first inner wall and extending from the deck to the bottom opening, and a first inner column extending from the deck to the bottom opening. The first side column, the second side column, and the first inner column cooperate to define a first driver channel from the bottom opening to one or more staple openings of the plurality of staple openings.

In an embodiment, the staple cartridge further includes a first surgical staple positioned in the first driver channel and a first driver positioned in the first driver channel. The first driver has a top saddle configured to engage the first surgical staple. The first surgical staple is positioned between the first driver and the deck. When the first driver is moved within the first driver channel from a first position that is closer to the bottom opening to a second position that is closer to the one or more staple openings, the first driver ejects the first surgical staple out of the one or more staple openings.

In an embodiment, the staple cartridge further includes a second surgical staple and a third surgical staple positioned in the first driver channel. The first driver further includes a second top saddle configured to engage the second surgical staple and a third top saddle configured to engage the third surgical staple. When the first driver is moved within the first driver channel from the first position to the second position, the first driver ejects the second surgical staple and the third surgical staple out of the one or more staple openings.

In an embodiment, the staple cartridge further includes a sled coupled to the elongated body, the sled having a central fin that extends upward into the central slot and a first angled fin that extends upward through the bottom opening. The sled is moveable from a proximal position to a distal position. When the sled is moved from the proximal position to the distal position, the first angled fin engages an angled bottom surface of the first driver and causes the first driver to move from the first position to the second position.

BRIEF DESCRIPTION OF THE DRAWINGS

The detailed description particularly refers to the following figures, in which.

DETAILED DESCRIPTION OF THE DRAWINGS

Figure 1:
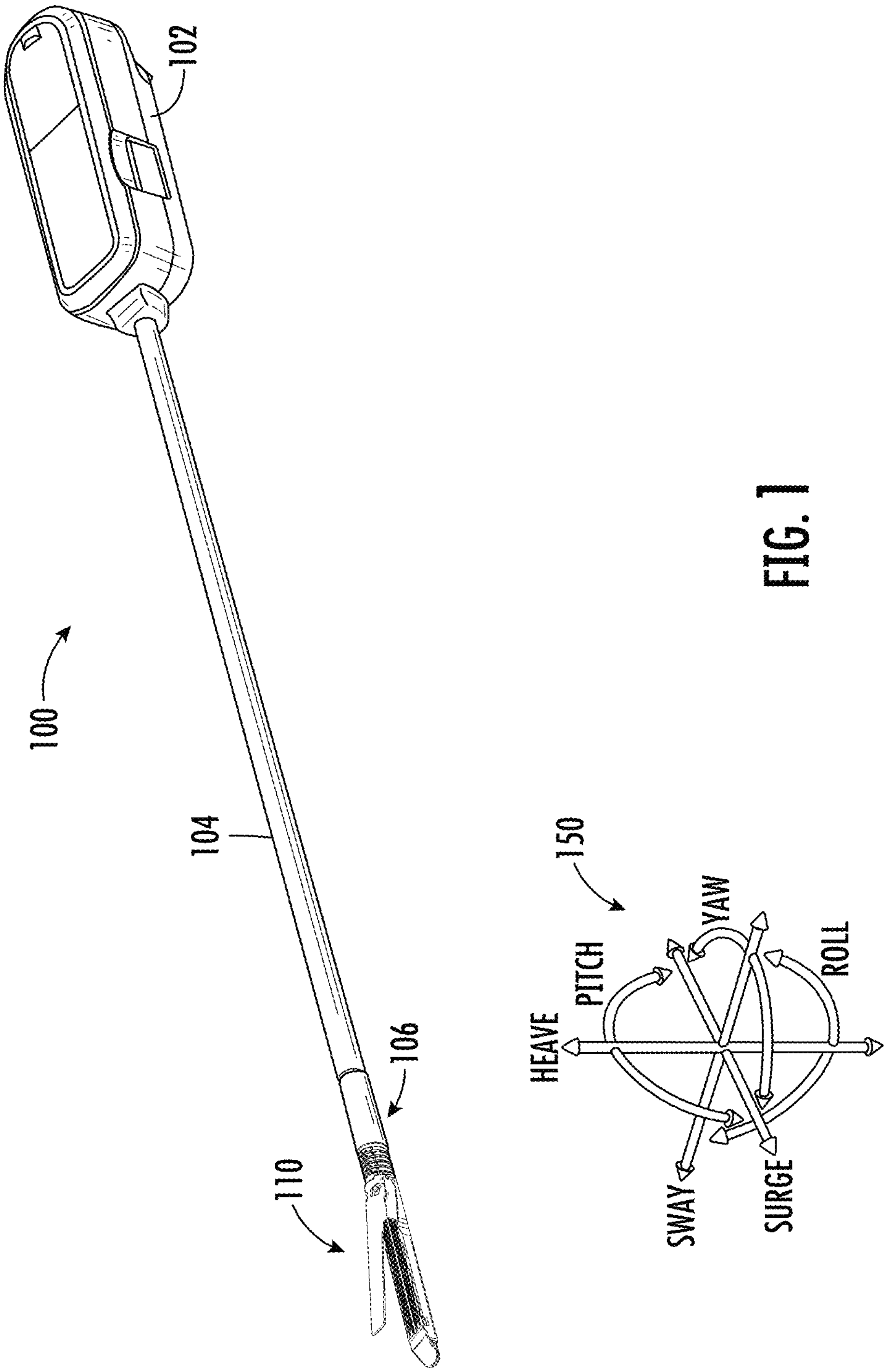
FIG. 1 is a perspective view of an embodiment of a surgical stapler configured for use with a robotic surgical system.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, et cetera, may be used throughout the specification in reference to the surgical instruments described herein as well as in reference to the patient's natural anatomy. Such terms have well-understood meanings in both the study of anatomy and the field of surgery. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C).

Similarly, items listed in the form of "at least one of A, B, or C" can mean (A); (B); (C); (A and B); (A and C); (B and C); or (A, B, and C).

Portions of the disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a surgical stapler or "endocutter" 100 is configured for use in minimally invasive surgery (MIS) procedures including, but not limited to, endoscopic and laparoscopic procedures. The surgical stapler 100 is configured to contemporaneously transect and staple tissue during the performance of such surgical procedures. Although the concepts presented below are described in regard to a surgical stapler, it should be appreciated that the presented concepts may be applicable to other types of surgical instruments configured to perform different surgical functions including, but not limited to, surgical scissors, tissue graspers, energy-based surgical instruments, clip appliers, needle drivers, and/or other surgical instruments.

The illustrative surgical stapler 100 includes a drive housing 102, an elongated shaft 104 that extends distally away from the drive housing 102, and an end effector 110 located at a distal end of the elongated shaft 104 opposite the drive housing 102. As discussed in more detail below, the surgical stapler 100 is embodied as a robotic surgical stapler and is configured to be used with a corresponding robotic surgical system. As such, the drive housing 102 includes coupling features that that facilitate the mounting of the drive housing 102 to a robotic arm of a robotic manipulator of the robotic surgery system as discussed below in regard to FIGS. 8 and 9. The mounting of the drive housing 102 to the robotic arm allows the robotic manipulator to control various functions of the surgical stapler 100, including the movement and "firing" of the end effector 110, as discussed in more detail below.

The elongated shaft 104 is sized and configured for use in minimally invasive surgery procedures. For example, the elongated shaft 104 has a length and diameter that is sized to allow the elongated shaft 104 to be inserted into a trocar or similar surgical tube to allow positioning of the end effector 110 into the patient's anatomical environment (e.g., the patient's abdominal cavity). Illustratively, the distal end of the elongated shaft 104 is coupled to the end effector 110 via an articulable joint 106, which allows the end effector 110 to be moved to different orientations and/or positions relative to the elongated shaft 104.

In the illustrative embodiment, the articulable joint 106 provides six degrees of freedom to the end effector 110. For example, as indicated by coordinate frame 150, the degrees of freedom of the end effector 110 may include three translational degrees (i.e., surge, heave, and sway) and three rotational degrees (i.e., roll, pitch, and yaw). The "surge" degree of freedom refers to forward and backward translational movement of the end effector 110 relative to the elongated shaft 104, the "heave" degree of freedom refers to upward and downward translational movement of the end effector 110 relative to the elongated shaft 104, and the "sway" degree of freedom refers to left and right translational movement of the end effector 110 relative to the elongated shaft 104. The "roll" degree of freedom refers to rotation of the end effector 110 along a longitudinal axis defined by the end effector 110, the "pitch" degree of freedom refers to upward and downward tilting of the end effector 110 relative to the elongated shaft 104, and the "yaw" degree of freedom refers to leftward or rightward turning of the distal end of the end effector 110 relative to the elongated shaft 104.

The elongated shaft 104 also houses a portion of an actuation system (not shown) to control the movement and activation (e.g., the "firing") of the end effector 110. The actuation system may include various articulation cables, push rods, firing rods, and/or other devices, which extend through the elongated shaft 104 from mechanisms located in the drive housing 102 to components of the articulable joint 106 and/or the end effector 110. In this way, the drive housing 102 is configured to control the movement and activation (i.e., the "firing") of the end effector 110.

Figure 2:
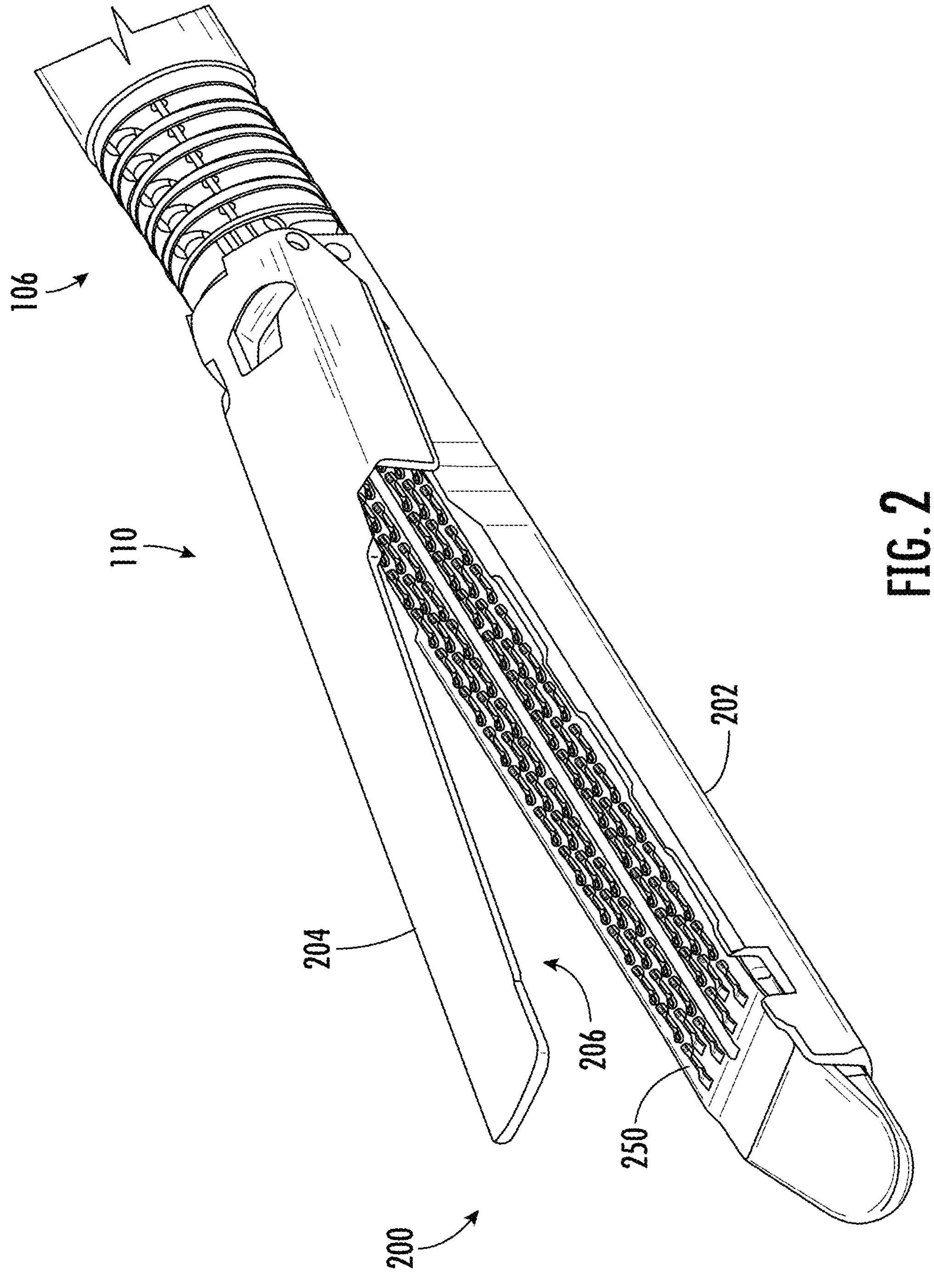
FIG. 2 is a perspective view of an embodiment of an end effector of the surgical stapler of FIG. 1.

Referring now to FIG. 2, the end effector 110 includes a jaw assembly 200, which illustratively includes a pair of jaws 202, 204 that oppose each other. The jaw 202 is illustratively embodied as a "cartridge" jaw and includes a channel 300 (see FIG. 3) configured to receive a staple cartridge 250. The jaw 204 is illustratively embodied as an "anvil" jaw and includes a bottom surface 206 having forming pockets configured to deform staples ejected from the staple cartridge 250.

The jaw assembly 200 is movable between an open state in which the anvil jaw 204 is positioned away from the cartridge jaw 202 and a closed state in which the anvil jaw 204 is positioned near or otherwise contacts the cartridge jaw 202. Illustratively, the anvil jaw 204 is configured to move toward and away from the cartridge jaw 202. However, in other embodiments, the cartridge jaw 202 may be configured to move relative to the anvil jaw 204 or both jaws 202, 204 may be configured to move toward or away from each other. Additionally, it should be appreciated that the open state may correspond to a degree of openness that is less than a fully opened position of the jaw assembly 200 and the closed state may correspond to a degree of closeness that is less than a fully closed position. That is, the closed state may, for example correspond to a minimal distance between the distal ends of the cartridge jaw 202 and the anvil jaw 204 and the open state may correspond to a maximum distance between the distal ends of the jaws 202, 204. However, in other embodiments, the open state may correspond to a fully opened position of the jaw assembly 200 and the closed state may correspond to a fully closed position of the jaw assembly 200.

Figure 3:
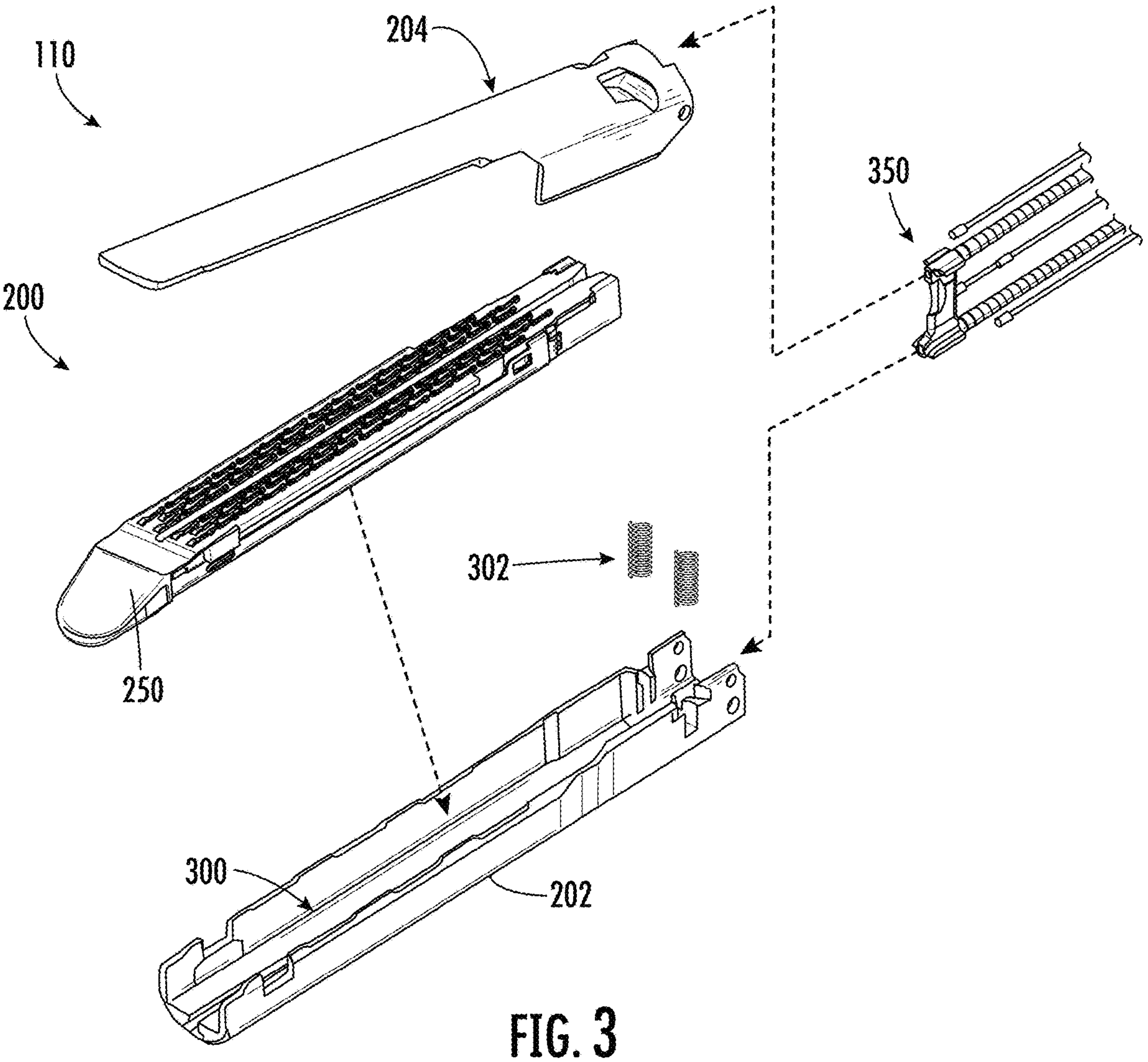
FIG. 3 is an exploded perspective view of and embodiment of a distal end of the surgical stapler of FIG. 1, including the end effector of FIG. 2.

As shown in FIG. 3, the jaw assembly 200 is biased in the open state by a pair of springs 302. That is, the springs 302 bias the anvil jaw 204 away from the cartridge jaw 202. However, actuation of the jaw assembly 200 overcomes the biasing force of the springs 302 to move the jaw assembly 200 from the open state to the closed state. When in the closed state, the end effector 110 can be "fired" to effect the cutting and stapling of tissue held within the jaw assembly 200

The end effector 110 also includes a I-beam 350, which is configured to translate forward during the firing of the end effector 110 from the proximal end of the jaws 202 toward the distal end of the jaws 202, 204. To do so, portions of the I-beam 350 are received in corresponding channels of the cartridge jaw 202 and the anvil jaw 204 as discussed in more detail below in regard to FIGS. 4 and 5. When the end effector 110 is fired, the I-beam 350 translates forward within the channels of the jaws 202, 204. The forward movement of the I-beam 350 may cause the anvil jaw 204 to move further downward toward or against the cartridge jaw 202 and clamp the jaw assembly in the closed state.

Figure 5:
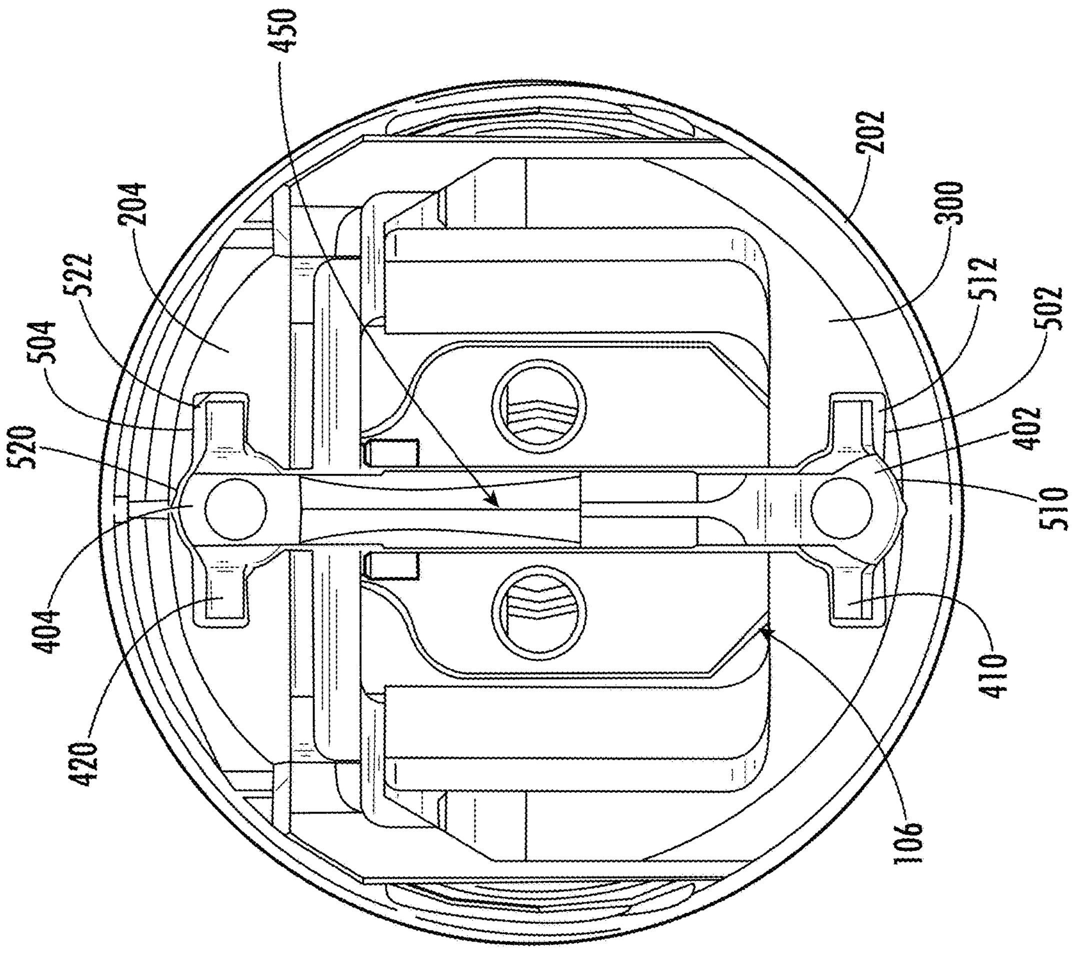
FIG. 5 is a cross-sectional view of the end effector of FIG. 1 in a closed state and showing the I-beam of FIG. 4 received in corresponding channels of the end effector of FIG. 2 with the knife of the I-beam extending between the corresponding channels.
Figure 4:
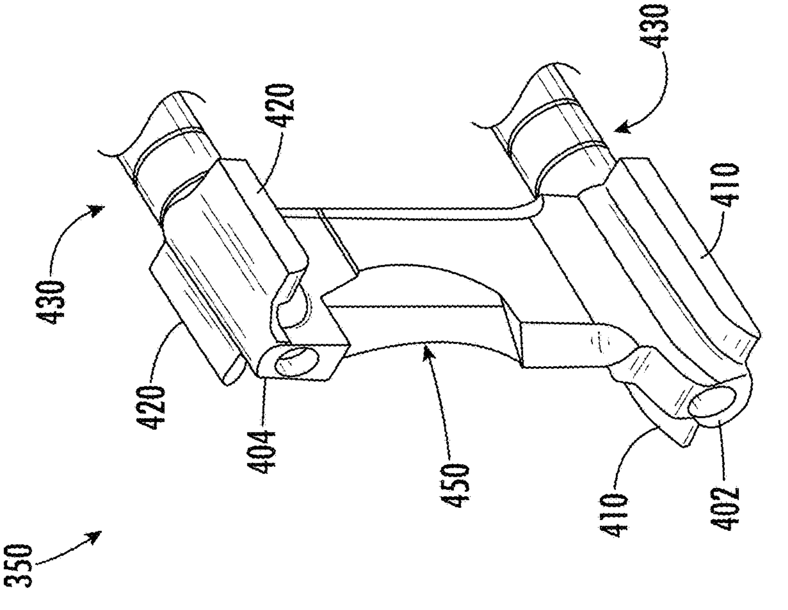
FIG. 4 is a perspective view of an embodiment of a I-beam of the end effector of FIG. 2, which includes a knife.

Referring now to FIGS. 4 and 5, the I-beam 350 includes a lower base 402, an upper base 404, and a knife 450 located between the upper and lower bases 402, 404. A pair of lower wings 410 extend laterally outward from the lower base 402. Similarly, a pair of upper wings 420 extend laterally outward from the upper base 404. A push rod 430 is coupled to each of the bases 402, 404 and to control mechanisms located in the drive housing 102. The control mechanisms of the drive housing 102 control movement of the push rods 430, which moves the I-beam 350 forward and backward within the jaw assembly 200.

When the end effector 110 is fired, the I-beam 350 moves within a lower I-beam channel 502 of the cartridge jaw 202 and an upper I-beam channel 504 of the anvil jaw 204 as shown in FIG. 5. The I-beam channel 502 of the cartridge jaw 202 includes a base channel 510 and a pair of wing channels 512, which are open to and in fluid communication with the base channel 510 and extend laterally outward therefrom. The lower base 402 of the I-beam 350 is received in and moves within the base channel 510 of the I-beam channel 502. Similarly, each lower wing 410 is received in and moves within a corresponding one of the wing channels 512. The I-beam channel 504 of the anvil jaw 204 also includes a base channel 520 and a pair of wing channels 522, which are open to and in fluid communication with the base channel 520 and extend laterally outward therefrom. The upper base 404 of the I-beam 350 is received in and moves within the base channel 520 of the I-beam channel 502. Similarly, each upper wing 420 is received in and moves within a corresponding one of the wing channels 522.

Figure 6:
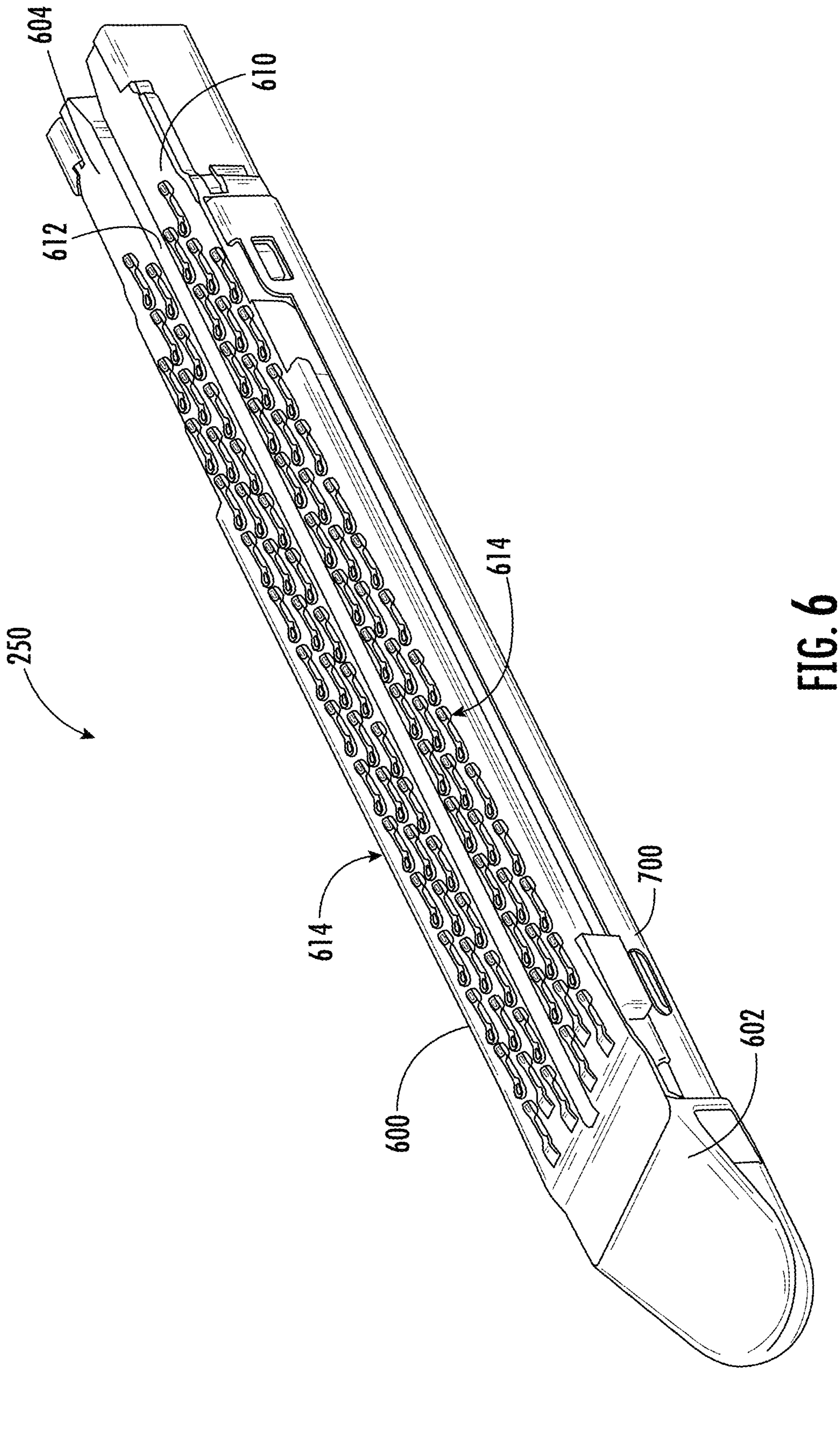
FIG. 6 is a perspective view of an embodiment of a stapler cartridge that may be inserted into the end effector of FIG. 2.
Figure 7:
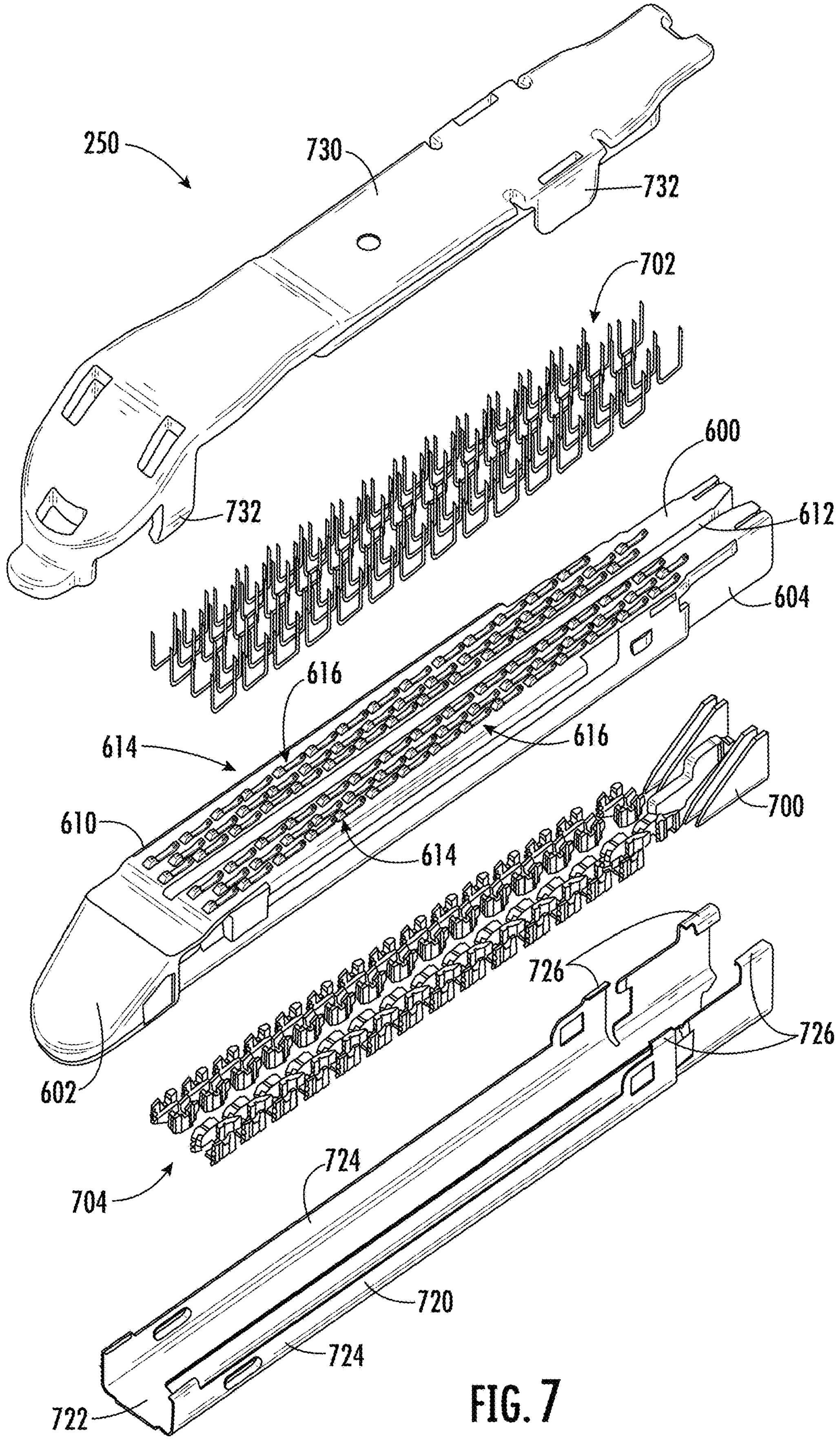
FIG. 7 is an exploded, perspective view of the stapler cartridge of FIG. 6.

Referring now to FIGS. 6 and 7, the illustrative staple cartridge 250 includes a cartridge body 600 having a distal end 602 and a proximal end 604. The cartridge body 600 also includes a deck 610 that extends from the proximal end 604 to the distal end 602. The deck 610 includes a longitudinal knife slot 612 that is located centrally on the deck 610 and extends from the distal end 602 toward the proximal end 604 of the cartridge body 600. During a firing stroke of the surgical stapler 100 (i.e., when the end effector is "fired"), the I-beam 350 transversed along the longitudinal knife slot 612 with the knife 450 of the I-beam 350 protruding upwardly from the longitudinal knife slot 612 to facilitate the transection of tissue captured within in the end effector 110 and held between the staple cartridge 250 and the anvil jaw 204.

A set of staple cavities 614 are defined in the deck 610 on either side of the longitudinal knife slot 612. A staple 702 is positioned in each of the staple cavities 614 and is supported by a corresponding staple driver 704. The staple cartridge 250 also includes a staple sled 700, which is initially located toward the proximal end 604 of the cartridge body 600 and is pushed toward the distal end 602 by the I-beam 350 when the end effector 110 is fired. The staple sled 700 lifts each staple driver 704 when the sled 700 comes into contact with the corresponding staple driver 704, which ejects the staple 702 associated with the corresponding staple driver 704 from the corresponding staple cavity 614. In the illustrative embodiment, the deck 610 includes staple guides or projections 616 that project upwardly from the deck 610 around each staple cavity 614. The staple guides 616 are configured to guide or control the legs of the staples 702 as the staples 702 are being ejected from the staple cavities 614. Illustratively, the staple guides 616 are located around the distal and proximal ends of each staple cavity 614, but may completely surround each staple cavity 614 or be located on only one end of each staple cavity 614 in other embodiments. The staple guides 616 may also form a set of "teeth" and be configured to grasp tissue held within the jaw assembly 200 to restrict movement of the tissue. In other embodiments, the deck 610 of the cartridge body 600 maybe devoid of any staple guides 616.

The staple cartridge 250 also includes a pan 720, which is attached to the cartridge body 600 and is configured to retain the staple drivers 704 and associated staples 702 within the cartridge body 600. Illustratively, the pan 720 is formed from a metallic material and includes a floor 722 and a pair of sidewalls 724 that extend upwardly from the floor 722 and wrap onto the sides of the cartridge body 600. The pan 720 includes a set of attachment tabs 726 that are configured to secure the pan 720 to the cartridge body 600.

Prior to use, the staple cartridge 250 includes a cover 730 attached to the cartridge body 600. The cover 730 is configured to cover the deck 610 of the staple cartridge 250 and includes a set of attachment tabs 732 configured to secure the cover 730 to the cartridge body 600. To prepare the staple cartridge 250 for use in the end effector 110, the cover 730 is removed from the cartridge body 600.

Although not illustrated in FIGS. 6 and 7, the staple cartridge 250 may also includes one or more electronic circuits or devices configured to perform one or more associated functions. For example, such electronic circuitry may include processors, digital storage devices, communication circuitry, sensor circuitry, and/or other electrical components.

Figure 8:
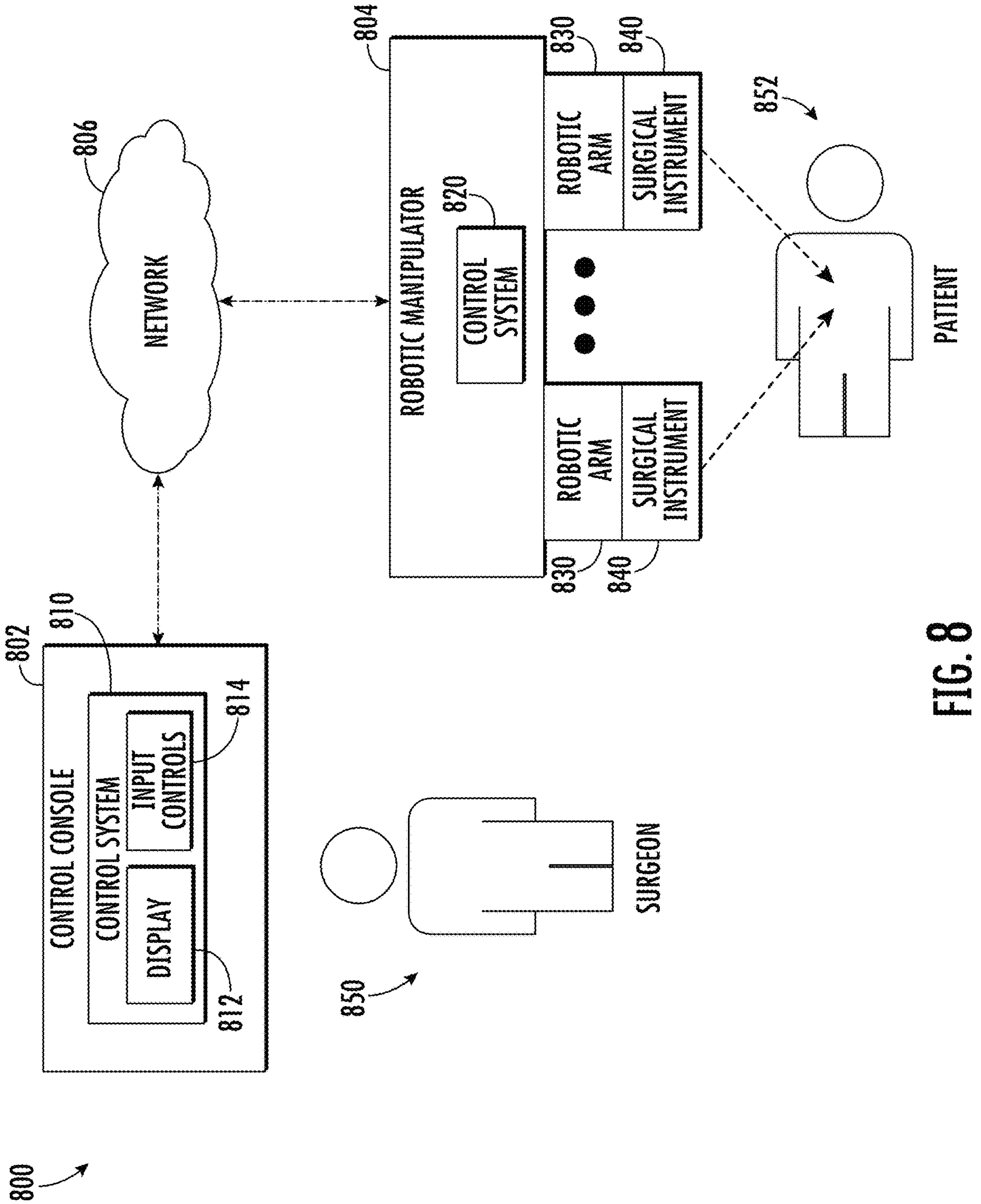
FIG. 8 is a simplified block diagram of an embodiment of a robotic surgical system including a control console and a robotic manipulator, with which the surgical stapler of FIG. 1 may be used.

Referring now to FIG. 8, as discussed above, the illustrative surgical stapler 100 is configured for use with a corresponding robotic surgical system 800. The robotic surgical system 800 includes a control console 802 and a robotic manipulator 804, which communicate with each other over a communication network 806. Although only a single control console 802 and a single robotic manipulator 804 is shown in FIG. 8, it should be appreciated that the robotic surgical system 800 may include additional control consoles 802 and/or robotic manipulators 804 in other embodiments.

The control console 802 is usable by a surgeon 850 to control the operation of the robotic manipulator 804. To do so, the control console 802 includes a control system 810. Illustratively, the control system 810 includes a display 812 and one or more input controls 814. However, it should be appreciated that the control system 810 may include additional electrical components and devices, such as a processor, a memory, and a communication subsystem to enable communications of the components of the control system 810, which are not illustrated in FIG. 8 for clarity.

The display 812 may be embodied as any type of display device capable of generating images viewable by the surgeon 850. In use, the display 812 may display images related to the surgical procedure being performed via the robotic manipulator 804. The displayed images may be obtained from, for example, an endoscopic camera operated by the robotic manipulator 804. Additionally, the display 812 may display information, including data determined by the control console 802 and/or the robotic manipulator 804, related to the surgical procedure (e.g., positional data of the robotic manipulator 804).

The input controls 814 are usable by the surgeon 850 to control the functionality of the robotic manipulator 804. The input controls 814 may be embodied as any type of input device capable of receiving a corresponding input from the surgeon 850. For example, the input controls 814 may include physical controllers, such as joy sticks, hand-held actuator modules, exoskeletal gloves, and/or other input devices. The input controls 814 may also include input devices other than hand-controlled devices such as foot pedals, vison tracking modules, and/or the like. In many embodiments, the input controls 814 are movable in multiple degrees of freedom to control the positioning and operation of the robotic manipulator 804.

The robotic manipulator 804 also includes a control system 820 and one or more robotic arms 830 to which surgical instruments 840 (e.g., the surgical stapler 100) may be mounted. In some embodiments, the robotic manipulator 804 may be mounted to a transport cart, sometimes referred to as an "arm cart," that enables mobility of the robotic manipulator 804 and the associated robotic arms 830.

The robotic arms 830 may include various articulable linkages and associated motors, which are controllable by the control console 802 to move the corresponding robotic arm 830 and any associated surgical instrument 840 to a desired position. For example, by manipulating an input control 814 of the control console 802, the surgeon 850 may control the positioning of a corresponding robotic arm 830, as well as the functionality of the associated surgical instrument 840 (e.g., the firing of the surgical stapler 100).

The control system 820 may be embodied as any type of controller or control circuit capable of controlling the functionality of the robotic manipulator including, for example, the movement of the robotic arms 830 and the activation of the surgical instruments 840 based on control signals received from the control console 802. To do so, the control system 820 may include various electrical components, circuits, and/or devices, such as a processor, a memory, and a communication subsystem to enable communications of the components of the control system 820, which are not illustrated in FIG. 8 for clarity.

In use, the robotic manipulator 804 is positioned in close proximity to a patient 852 requiring surgery. The robotic manipulator 804 may be locked or mounted in place for the duration of the surgery. The surgeon 850 may then manipulate the input controls 814 to position one or more robotic arms 830 and associated surgical instruments 840 into a desired position. For example, the surgeon 850 may position a robotic arm 830 such that an associated surgical instrument 840 is inserted through a trocar or similar elongated passageway into the anatomical environment (e.g., the abdominal cavity of the patient 852). Once so positioned, some surgical instruments 840 (e.g., an endoscope) may be locked into position to avoid unintended repositioning.

The network 806 may be embodied as any type of wired and/or wireless network or set of communication links capable of facilitating communications between the control console 802 and the robotic manipulator 804. To do so, the network 806 enable such communications using any suitable data communication specification and/or protocol. As such, in some embodiments, the network 806 may include additional devices, such as additional computers, routers, stations, and/or switches, to facilitate such communications between the control console 802 and the robotic manipulator 804.

Figure 9:
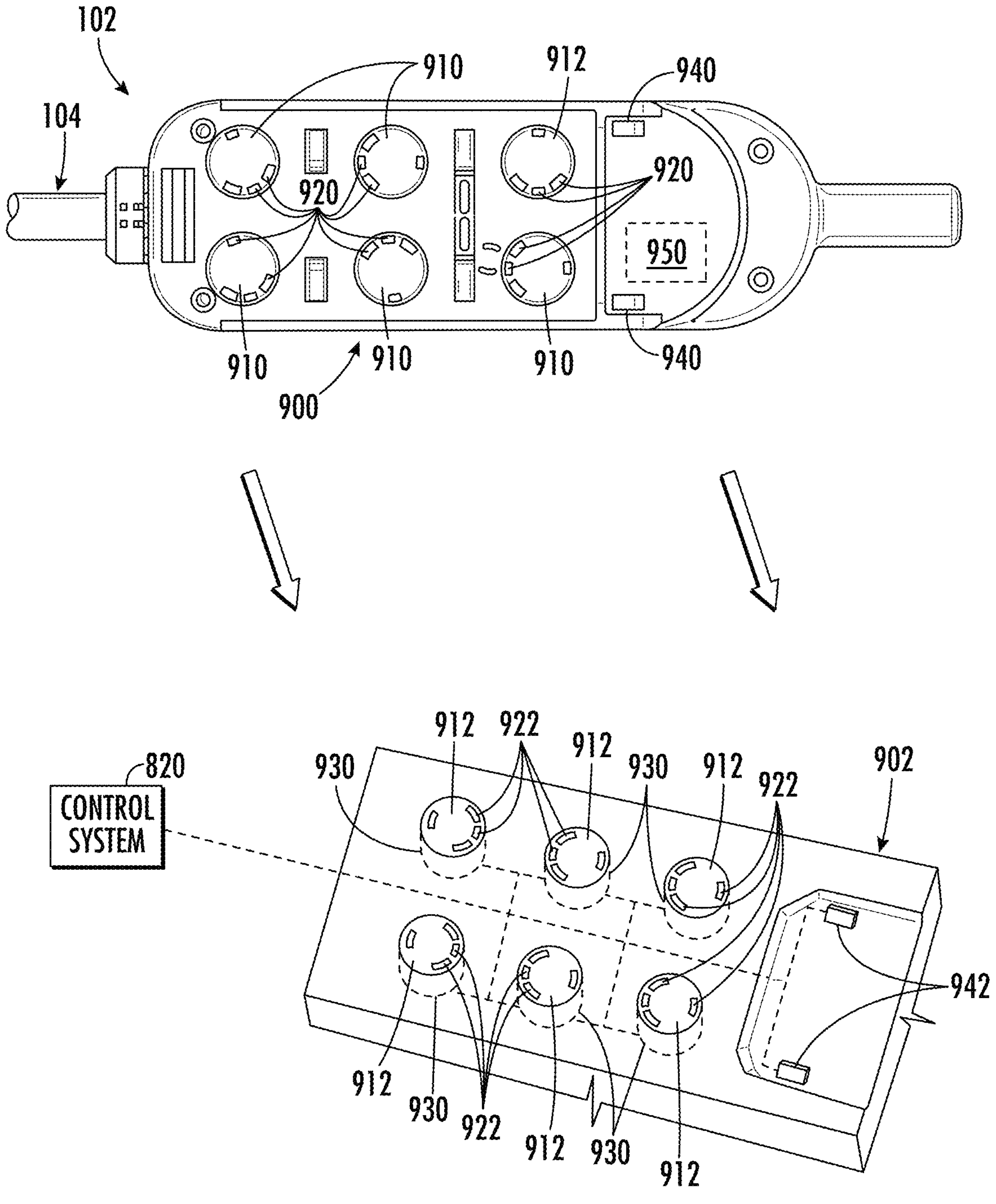
FIG. 9 is a diagrammatic view of an embodiment of a tool interface located on a bottom side of a drive housing of the surgical stapler of FIG. 1 being coupled to an arm interface located on a robotic arm of the robotic manipulator of the robotic surgical system of FIG. 8.

Referring now to FIG. 9, as discussed above, the surgical stapler 100 (and other surgical instruments 840) is configured to be mounted to a robotic arm 830 of the robotic manipulator 804. To facilitate such mounting, the drive housing 102 of the surgical stapler 100 includes a tool interface 900 located on a bottom side of the drive housing 102. The tool interface 900 is configured to mate with an arm interface 902 of the corresponding robotic arm 830 to couple the surgical stapler 100 to the robotic arm 830. The coupling of the surgical stapler 100 to the robotic arm 830 may be further facilitated via various mechanical, magnetic, and/or electrical features. In some embodiments, a sterile barrier may also be used between the surgical stapler 100 and the robotic arm 830. It should be appreciated that mounting of the surgical stapler 100 to the robotic arm places the surgical stapler 100 into communication and under the control of the control system 820 of the robotic manipulator 804, which is controlled by the control console 802 as discussed above.

The tool interface 900 includes a set of input pucks 910, which are manipulable to control functions of the surgical stapler 100 such as the positioning and firing of the end effector 110. Each input puck 910 is configured to mate with a corresponding puck driver 912 of the arm interface 902. To do so, each input puck 910 includes mating features 920 that are configured to mate with mating features 922 of the corresponding puck driver 912. In the illustrative embodiment, the mating features 920 of the input pucks 910 are embodied as tabs or protrusions that extend upwardly from the corresponding input puck 910, and the mating features 922 of the puck drivers 912 are embodied as recesses configured to receive the tabs/protrusions 920 of the input pucks 910. In other embodiments, however, the mating features 920 of the input pucks 910 may be embodied as recesses and the mating features 922 of the puck drivers 912 may be embodied as tabs/protrusions.

The arm interface 902 includes an electric motor 930 operatively coupled to each puck driver 912. Each electric motor 930 is communicatively coupled to and controlled by the control system 820. Actuation of a given electric motor 930 causes actuation of the associated puck driver 912, which causes actuation of the corresponding input puck 910. For example, rotation of an electric motor 930 causes rotation of the associated puck driver 912, which causes rotation of the corresponding input puck 910. In this way, the positioning and activation (e.g., "firing") of the end effector 110 of the surgical stapler 100 may be controlled via actuation of the puck drivers 912 and associated input pucks 910.

The tool interface 900 also includes a set of electrical connectors 940, which are configured to mate with corresponding electrical connectors 942 of the arm interface 902. The electrical connectors 940, 942 provide electrical communication between the surgical stapler 100 and the robotic manipulator 804. However, in other embodiments, the surgical stapler 100 and the robotic manipulator 804 may be configured to communicate in other ways, such as via wireless communications. In some embodiments, the tool interface 900 may also include a control system 950. In such embodiments, the control system 950 may be configured to control and/or monitor various operations the surgical stapler 100. The control system 950 may include various electrical components, circuits, and/or devices, such as a processor, a memory, and a communication subsystem to enable communications of the components of the control system 950, which are not illustrated in FIG. 9 for clarity.

Figure 10:
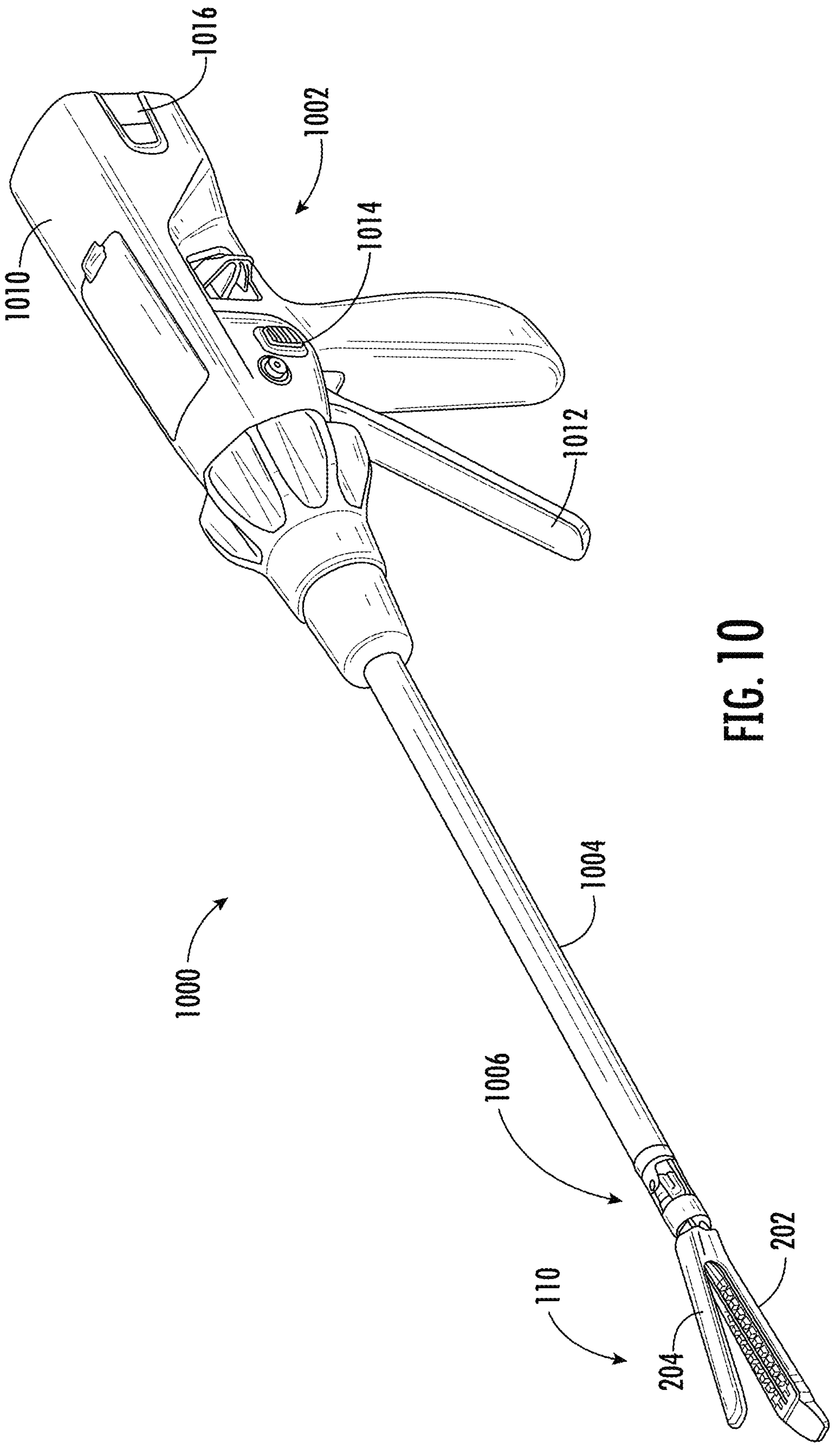
FIG. 10 is a perspective view of an embodiment of a hand-held surgical stapler including the end effector of FIG. 2.

Although the illustrative surgical stapler 100 shown and described above in regard to FIGS. 1-9 is configured for use in a robotic surgical system, the features and concepts of the surgical stapler 100 described above and below may be applicable to hand-held surgical staplers and devices. For example, as shown in FIG. 10, the end effector 110 may be incorporated into a hand-held surgical stapler 1000. The surgical stapler 1000 includes a handle 1002 and an elongated shaft 1004 extending from the handle 1002. The distal end of the elongated shaft 1004 is coupled to the end effector 110 via an articulable joint 1006, which may be substantially similar to the articulable joint 106 described above.

The handle 1002 includes a handle housing 1010 and a trigger assembly 1012 movable connected to the handle housing 1010. The trigger assembly is operable by a surgeon to move the jaw assembly 200 of the end effector 110 from the open state to the closed state as discussed above. The handle 1002 also includes one or more activation triggers 1014 to, for example, initiate the firing of the end effector 110 when in the closed state. A replaceable and/or rechargeable battery pack 1016 is coupled to an end of the handle housing 1010 and provide power to the electrical components located within the handle housing 1010.

Figure 11:
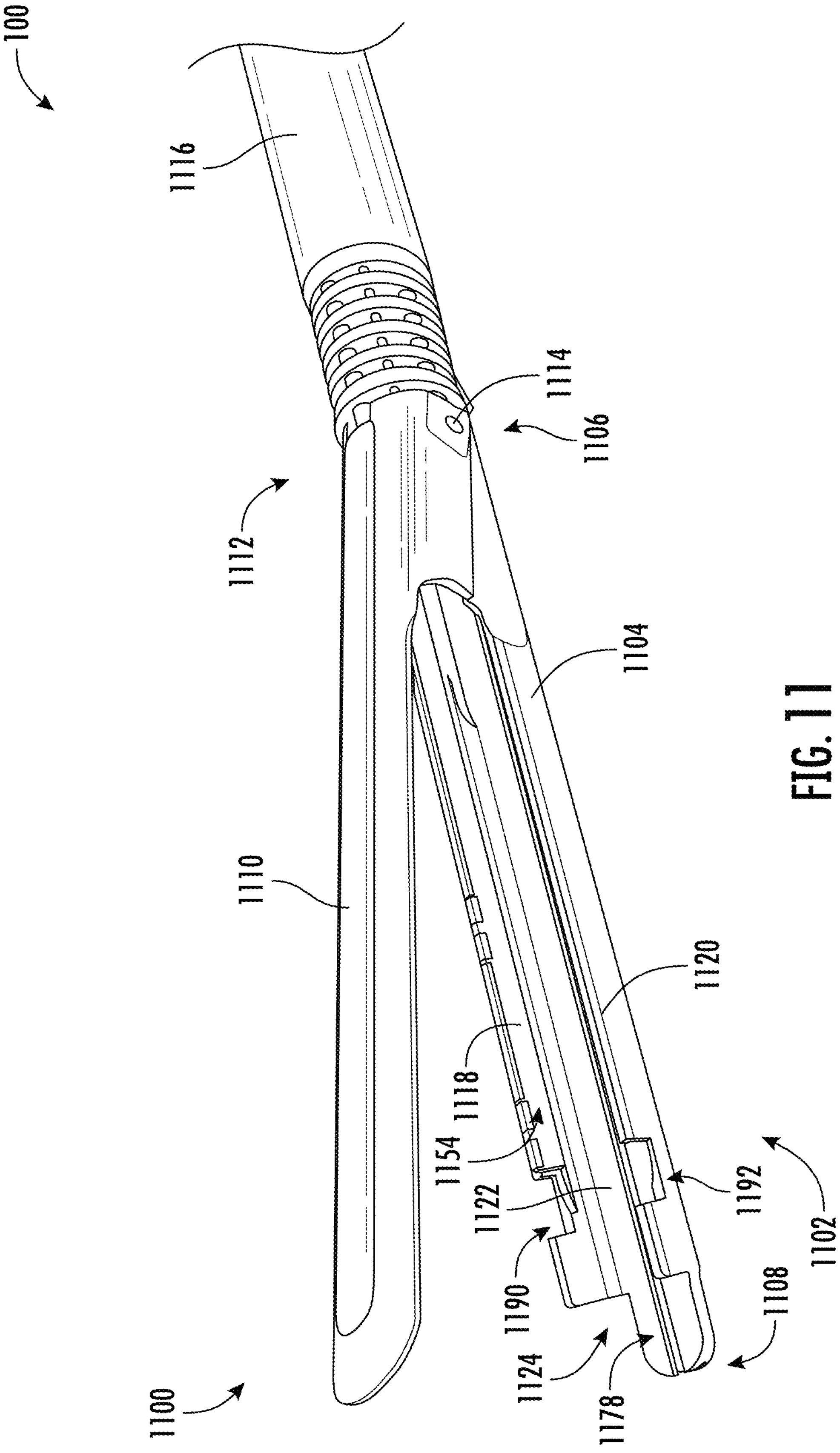
FIG. 11 is a perspective view of an end effector for a surgical instrument of the system of FIGS. 1-10.
Figure 12:
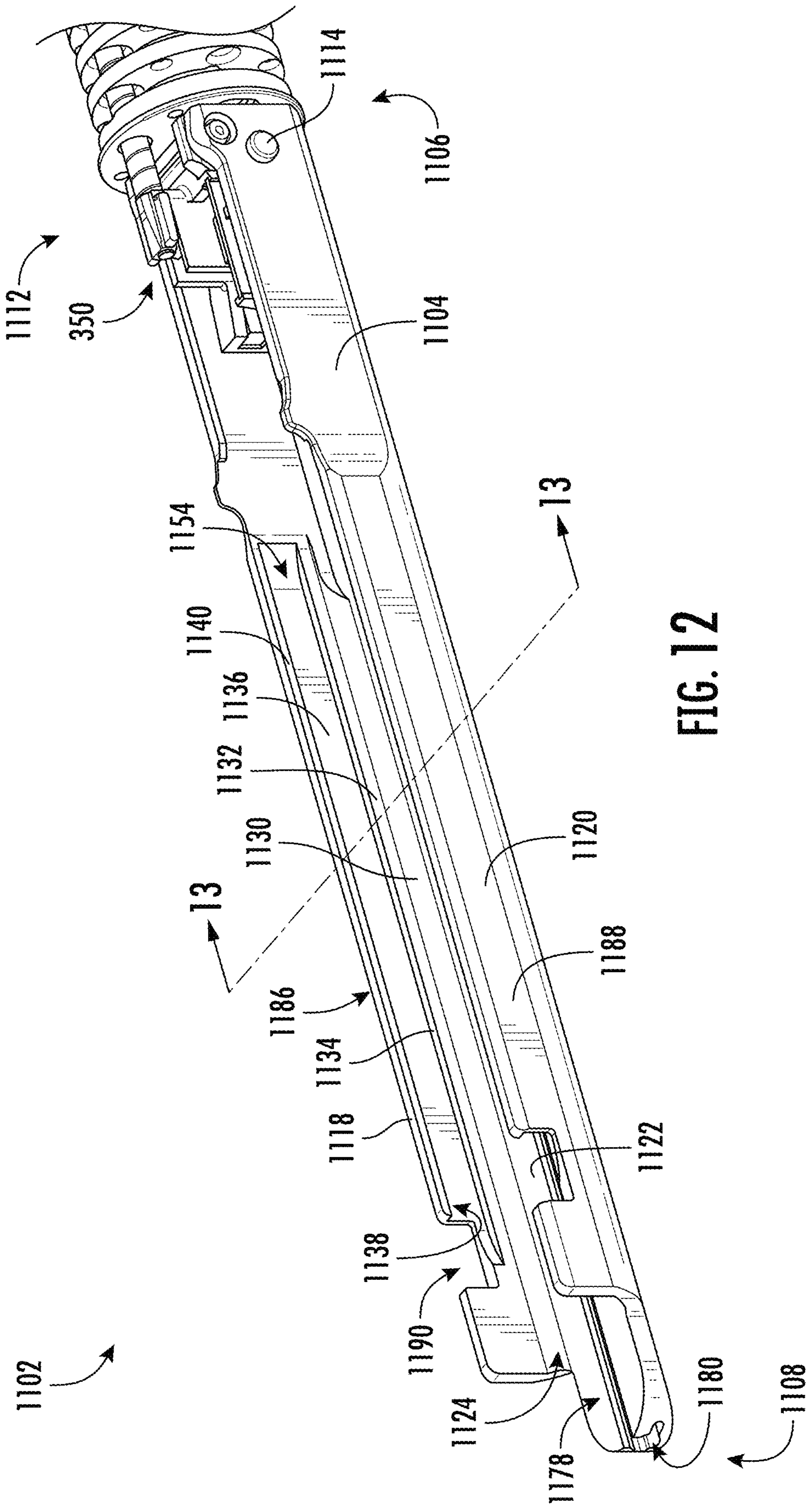
FIG. 12 is a perspective view of a lower jaw of the end effector of FIG. 11.
Figure 13:
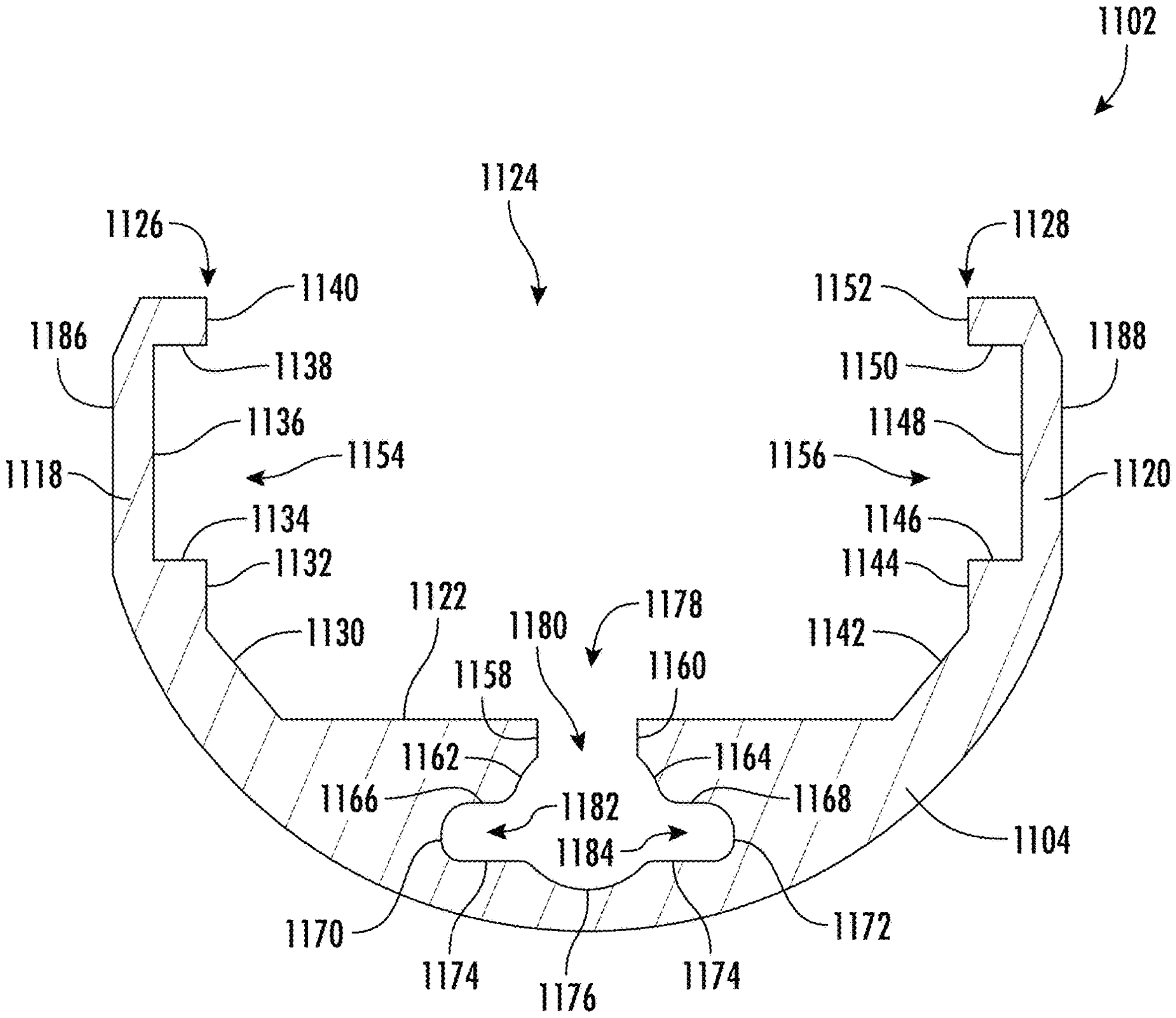
FIG. 13 is a cross-sectional view of the lower jaw of FIG. 12.
Figure 14:
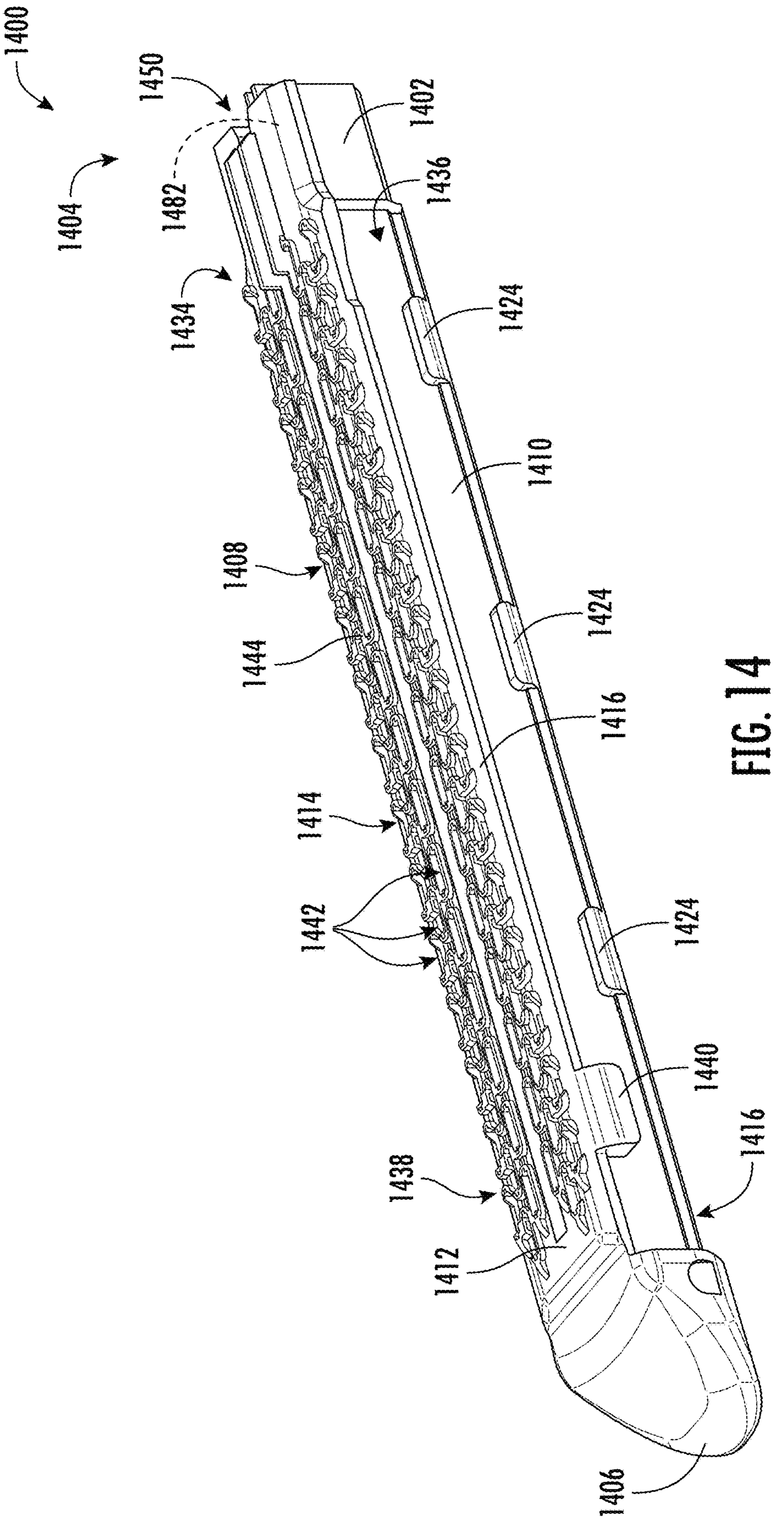
FIG. 14 is a perspective view of a reload cartridge that may be used with the end effector of FIGS. 11-13.

Referring now to FIGS. 11-13, in an illustrative embodiment, the end effector 110 of the surgical stapler 100 and/or the hand-held surgical stapler 1000 may be embodied as an end effector 1100 having a cartridge jaw 1102 including an elongated body 1104 that extends from a proximal end 1106 to a distal end 1108. The end effector 1100 may be similar to an end effector 110 of a surgical stapler 100 and/or a handheld surgical stapler 1000, and thus may include one or more components similar to the end effector 110 as described above.

Illustratively, the cartridge jaw 1102 is coupled to an anvil jaw 1110 at a hinge 1112 by a pin 1114. A shown, the hinge 1112 is positioned toward the proximal end 1106 of the cartridge jaw 1102. Accordingly, and as described further below, the anvil jaw 1110 may pivot about the pin 1114 and rotate from an open position as shown in FIG. 11 to a closed position in which the anvil jaw 1110 contacts the cartridge jaw 1102, grasps tissue between the anvil jaw 1110 and the cartridge jaw 1102, and/or comes near the cartridge jaw 1102.

As shown, the proximal end 1106 of the cartridge jaw 1102 is further coupled to an elongated shaft 1116, which may be coupled to a robotic tool interface of the surgical stapler 100 and/or a handpiece of the hand-held surgical stapler 1000, as described above. Accordingly, the shaft 1116 further includes a drivetrain for actuating the end effector 1100, such as a spring driveshaft, one or more pushrods, shafts, and/or other actuators.

The cartridge jaw 1102 also includes a pair of parallel, opposing side walls 1118, 1120 that extend from the hinge 1112 toward the distal end 1108. A floor 1122 connects the side walls 1118, 1120, and extends from the hinge 1112 to the distal end 1108. The side walls 1118, 1120 and the floor 1122 cooperate to define a channel 1124, which also extends from the hinge 1112 to the distal end 1108.

Each of the side walls 1118, 1120 includes a respective inner surface 1126, 1128 that faces the channel 1124. As best shown in FIG. 13, the inner surface 1126 includes an angled chamfer 1130 that extends upward from the floor 1122. A wall foot 1132 extends upward from the chamfer 1130, a ledge 1134 extends outward from the wall foot 1132, an inner groove surface 1136 extends upward from the ledge 1134, another ledge 1138 extends inward from the inner groove surface 1136, and a wall header 1140 extends upward from the ledge 1138. Similarly, the inner surface 1128 includes an angled chamfer 1142 that extends upward from the floor 1122. A wall foot 1144 extends upward from the chamfer 1142, a ledge 1146 extends outward from the wall foot 1144, an inner groove surface 1148 extends upward from the ledge 1146, another ledge 1150 extends inward from the inner groove surface 1148, and a wall header 1152 extends upward from the ledge 1150.

The ledge 1134, the inner groove surface 1136, and the ledge 1138 of the inner surface 1126 cooperate to define a groove 1154 within the side wall 1118. Similarly, the ledge 1146, the inner groove surface 1148, and the ledge 1150 of the inner surface 1128 cooperate to define a groove 1156 within the side wall 1120. Each of the grooves 1154, 1156 is in communication with the channel 1124.

Although illustrated in FIGS. 11-13 as including a pair of grooves 1154, 1156 defined in the respective side walls 1118, 1120, it should be understood that in other embodiments the end effector 1100 may include a different number and/or arrangement of grooves defined in the side walls 1118, 1120. For example, in an embodiment, the cartridge jaw 1102 may be asymmetric, with a groove 1154 defined in the side wall 1118, but without a groove 1156 defined in the side wall 1120. Continuing that example, the inner surface 1128 may include the angled chamfer 1142, and the wall foot 1144 may extend all of the way to the wall header 1152, without including any of the ledges 1146, 1150 or the inner groove surface 1148. Similarly, in another embodiment, the cartridge jaw 1102 may include a groove 1156 defined in the side wall 1120 but may be without the groove 1154 defined in the side wall 1118.

Referring again to the embodiment shown in FIGS. 11-13, and as best shown in FIG. 13, the floor 1122 includes a pair of parallel slot walls 1158, 1160 extending downward from the floor 1122. The slot walls 1158, 1160 extend along the length of the cartridge jaw 1102, from the proximal end 1106 to the distal end 1108. A pair of curved walls 1162, 1164 extend downward and outward in opposite directions from the respective slot walls 1158, 1160. A pair of inner cutout walls 1166, 1168 extend outward in opposite directions from the respective curved walls 1162, 1166. Each of the respective inner cutout walls 1166, 1168 extend to a respective pair of curved end walls 1170, 1172. The curved end walls 1170, 1172 curve inwardly, and are coupled to a slot floor 1174, which connects the curved end walls 1170, 1172. A curved depression 1176 is defined in the slot floor 1174.

As shown, the slot walls 1158, 1160, the curved walls 1162, 1164, the inner cutout walls 1166, 1168, the curved end walls 1170, 1172, and the slot floor 1174 cooperate to define a slot 1178. The slot 1178 is in communication with the channel 1124 via an opening defined between the slot walls 1158, 1160. As shown, the slot 1178 further includes a slot bore 1180 defined by the curved walls 1162, 1164 and the depression 1176 in the slot floor 1174. The slot 1178 further includes a pair of slot side annexes 1182, 1184 defined by the inner cutout walls 1166, 1168, the curved end walls 1170, 1172, and the slot floor 1174, respectively. The slot 1178 further includes a pair of slot side annexes 1182, 1184. The slot side annex 1182 is defined by the inner cutout wall 1166, the curved end wall 1170 and the slot floor 1174, and the slot side annex 1184 is similarly defined by the inner cutout wall 1168, the curved end wall 1172 and the slot floor 1174. As described further below, the slot 1178 is configured to receive the I-beam 350 of the end effector 1100. For example, a lower beam or wing 410 of the I-beam 350 may be received in the slot side annexes 1182, 1184.

Referring again to FIGS. 11-13, each of the side walls 1118, 1120 include respective flat outer side surface 1186, 1188. A pair of notches 1190, 1192 are further defined in the respective side walls 1118, 1120. As described further below, the notches 1190, 1192 may receive corresponding keys of a staple reload cartridge, allowing the cartridge to be easily positioned within the cartridge jaw 1102.

Additionally, in some embodiments, a distance between the outer side surfaces 1186, 1188 may be constrained to fit within the dimensions of pre-existing surgical instruments, for example to fit within a standardized trocar or other aperture used with surgical instruments. Accordingly, the end effector 1100 may be used as an improved replacement for existing end effectors in surgical instruments.

Referring now to FIGS. 14-17, a staple reload cartridge 1400 may be used with the end effector 1100 of FIGS. 11-13. The cartridge 1400 may be similar to a cartridge 250 of the surgical stapler 100 described above, and thus may include one or more components similar to the cartridge 250.

The illustrative cartridge 1400 includes an elongated body 1402 extending from a proximal end 1404 to a distal nose 1406. A pair of parallel side walls 1408, 1410 extend from the proximal end 1404 to the distal nose 1406. A deck 1412 is connected to the top of each of the parallel side walls 1408, 1410, and extends from the proximal end 1404 to the distal nose 1406. The deck 1412 connects the side walls 1408, 1410 at the distal nose 1406 at least. Each of the side walls 1408, 1410 extends downward to a corresponding bottom surface 1409, 1411.

Figure 15:
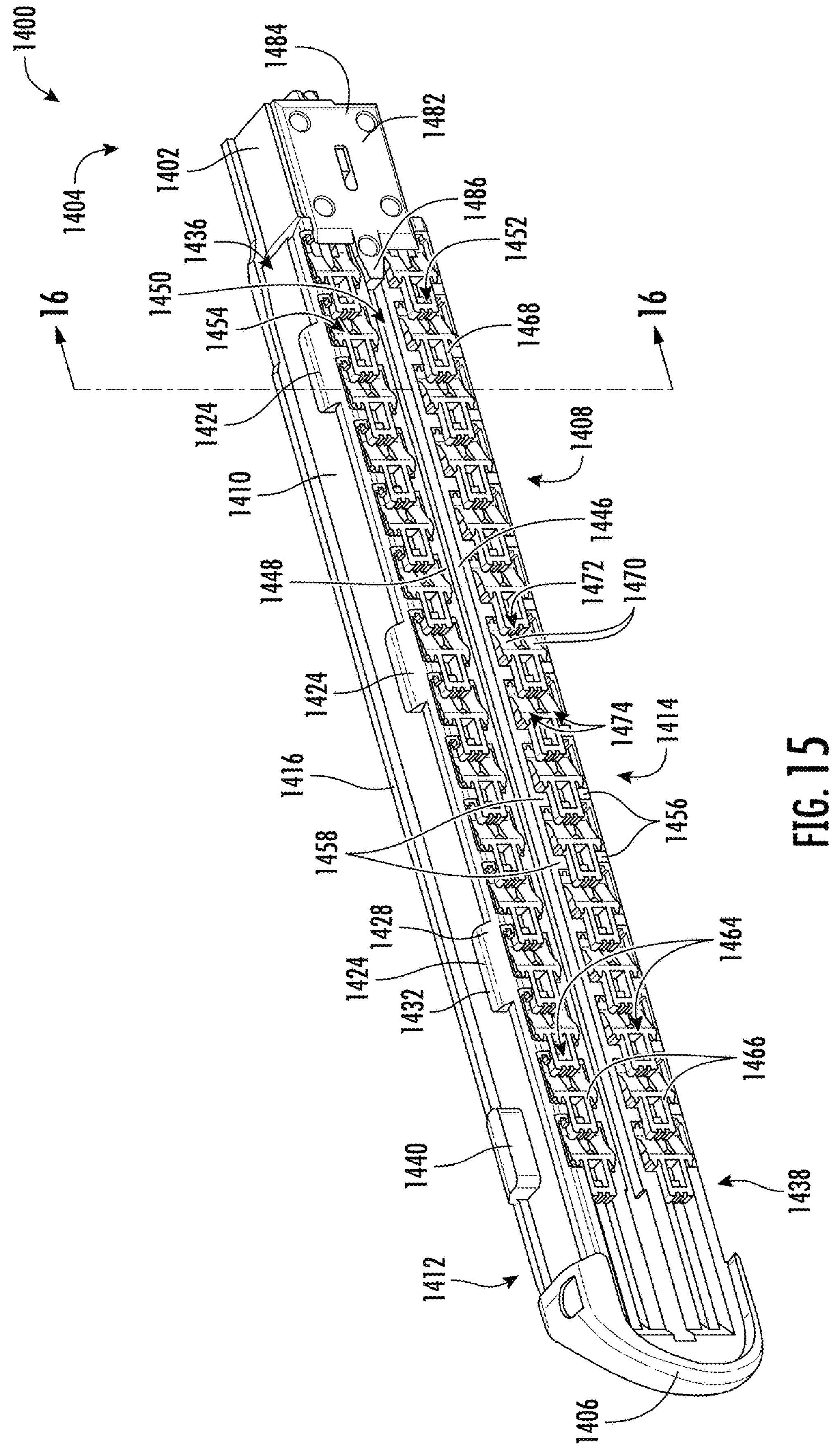
FIG. 15 is a bottom perspective view of the reload cartridge of FIG. 14.
Figure 16:
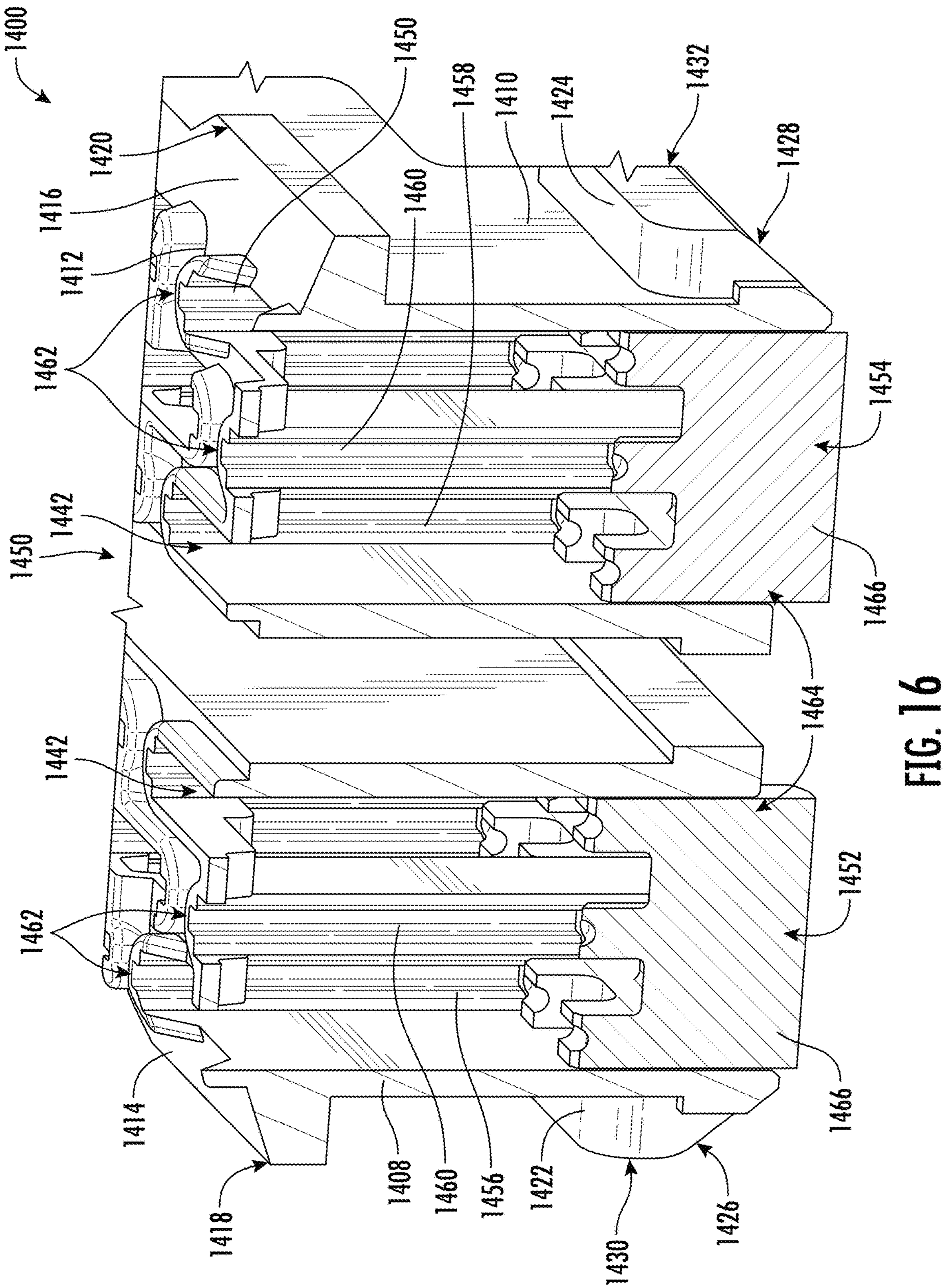
FIG. 16 is a cross-sectional view of the reload cartridge of FIGS. 14-15.

As best shown in FIG. 16, the side wall 1408 includes a top rail 1414 that extends outward from the side wall 1408 at a top of the side wall 1408. The top rail 1414 includes a flat outer surface 1418. As shown in FIGS. 15-16, the side wall 1408 further includes a bottom rail 1415 that extends outward from the side wall 1408 at a bottom of the side wall 1408. The side wall 1408 further includes multiple bottom pads 1422 that extend outward from the side wall 1408 at the bottom of the side wall 1408, extending outward further than the bottom rail 1415. Each of the bottom pads 1422 includes a corresponding bottom chamfer 1426 and a flat outer surface 1430.

Similarly, and as shown in FIGS. 14-17, the side wall 1410 also includes a top rail 1416 that extends outward from the side wall 1410 at a top of the side wall 1410. The side wall 1410 further includes a bottom rail 1417 that extends outward from the side wall 1410 at a bottom of the side wall 1410. The top rail 1416 includes a flat outer surface 1420. The side wall 1410 further includes multiple bottom pads 1424 that extend outward from the side wall 1410 at the bottom of the side wall 1410, extending outward further than the bottom rail 1417. Each of the bottom pads 1424 includes a corresponding bottom chamfer 1428 and a flat outer surface 1432.

The illustrative cartridge 1400 shown in FIGS. 14-17 includes three bottom pads 1422 on the side wall 1408 and three bottom pads 1424 on the side wall 1410. However, it should be understood that other embodiments of the cartridge 1400 may include a different number and/or arrangement of bottom pads 1422, 1424. For example, in an embodiment the cartridge 1400 may include a fewer number of pads 1422, 1424 on each side wall 1408, 1410 (e.g., two pads 1422, 1424 on each respective side wall 1408, 1410 or a single pad 1422, 1424 on each respective side wall) or a larger number of pads 1422, 1424 on each respective side wall 1408, 1410. As shown in FIGS. 14-17, each of the top rails 1414, 1416 extends the entire length of the cartridge body 1402 from the proximal end 1404 to the distal nose 1406. In contrast, the bottom pads 1422, 1424 may not cover the entire length of the side walls 1408, 1410. Additionally or alternatively, in some embodiments the cartridge 1400 may include one or more bottom pads 1422, 1424 that do over the entire length of the side walls 1408, 1410.

Referring again to FIGS. 14-17, the top rail 1414, the side wall 1408, and the bottom pads 1422 cooperate to define a groove 1434 positioned on the outside of the side wall 1408. Similarly, the top rail 1416, the side wall 1410, and the bottom pads 1424 cooperate to define a groove 1438 positioned on the outside of the side wall 1410. Additionally a pair of tabs 1438, 1440 extend outwardly from the respective side walls 1408, 1410 and top rails 1414, 1416 near the distal nose 1406. As described further below, the tabs 1438, 1440 may be received in corresponding notches 1190, 1192 defined in the cartridge jaw 1102 of the end effector 1100, which may key or otherwise locate and align the cartridge 1400 within the end effector 1100.

The cartridge 1400 further includes multiple staple openings 1442 defined through the deck 1412. Each of the staple openings 1442 may be embodied as an oval-shaped aperture or other opening through the deck 1412. As described further below, each of the staple openings 1442 is sized to allow a surgical staple to be ejected through the staple opening 1442. In some embodiments, the deck 1412 may further include one or more deck relief features 1444 extending upward from the deck 1412 and in some embodiments surrounding one or more of the staple openings 1442. In use, the deck relief features 1444 may increase grip on tissue held between the deck 1412 and the anvil jaw 1110 of the end effector 100.

As best shown in FIGS. 15-16, the cartridge 1400 further includes a pair of parallel inner walls 1446, 1448 extending downward from the deck 1412. Each of the inner walls 1446, 1448 extend from the proximal end 1404 of the body 1402 to a position near the distal nose 1406. The inner walls 1446, 1448 cooperate to define a central slot 1450 extending through the body 1402 from the proximal end 1404 to that position near the distal nose 1406. The inner wall 1446 and the side wall 1408 cooperate to define an elongated bottom opening 1452 in the cartridge body 1402, and, similarly, the inner wall 1448 and the side wall 1410 cooperate to define an elongated bottom opening 1454 in the cartridge body 1402.

The cartridge 1400 further includes multiple side columns 1456 coupled to the side walls 1408, 1410, and extending from the deck 1412 to the openings 1452, 1454. Each of the side columns 1456 may extend downward slightly past the bottom surface 1409, 1411 of the corresponding side wall 1408, 1410. Similarly, the cartridge 1400 also includes multiple side columns 1458 coupled to the inner walls 1446, 1448 and extending from the deck 1412 to the openings 1452, 1454. As shown, the side columns 1458 do not extend downward past the bottom surfaces 1409, 1411. Each of the side columns 1456, 1458 is positioned within an interior of the cartridge body 1402. That is, the side columns 1456 are positioned on an inward surface of the side walls 1408, 1410, facing the respective inner walls 1446, 1448 and the side columns 1458 are positioned on an outward surface of the inner walls 1446, 1448, facing the respective side walls 1408, 1410. The cartridge 1400 further includes multiple inner columns 1460 extending downward from the deck 1412 toward the openings 1452, 1454. Each of the inner columns 1460 is positioned within the interior of the cartridge body 1402, between the side wall 1408 and the inner wall 1446, or between the side wall 1410 and the inner wall 1448.

Each of the columns 1456, 1458, 1460 includes a vertical groove 1462 defined on its proximal and distal sides. The vertical grooves 1462 extend the length of the respective columns 1456, 1458, 1460 from the deck 1412 to the openings 1452, 1454. The columns 1456, 1458, 1460 cooperate to define multiple driver channels 1464 that extend from the openings 1452, 1454 upward to the deck 1412.

Figure 17:
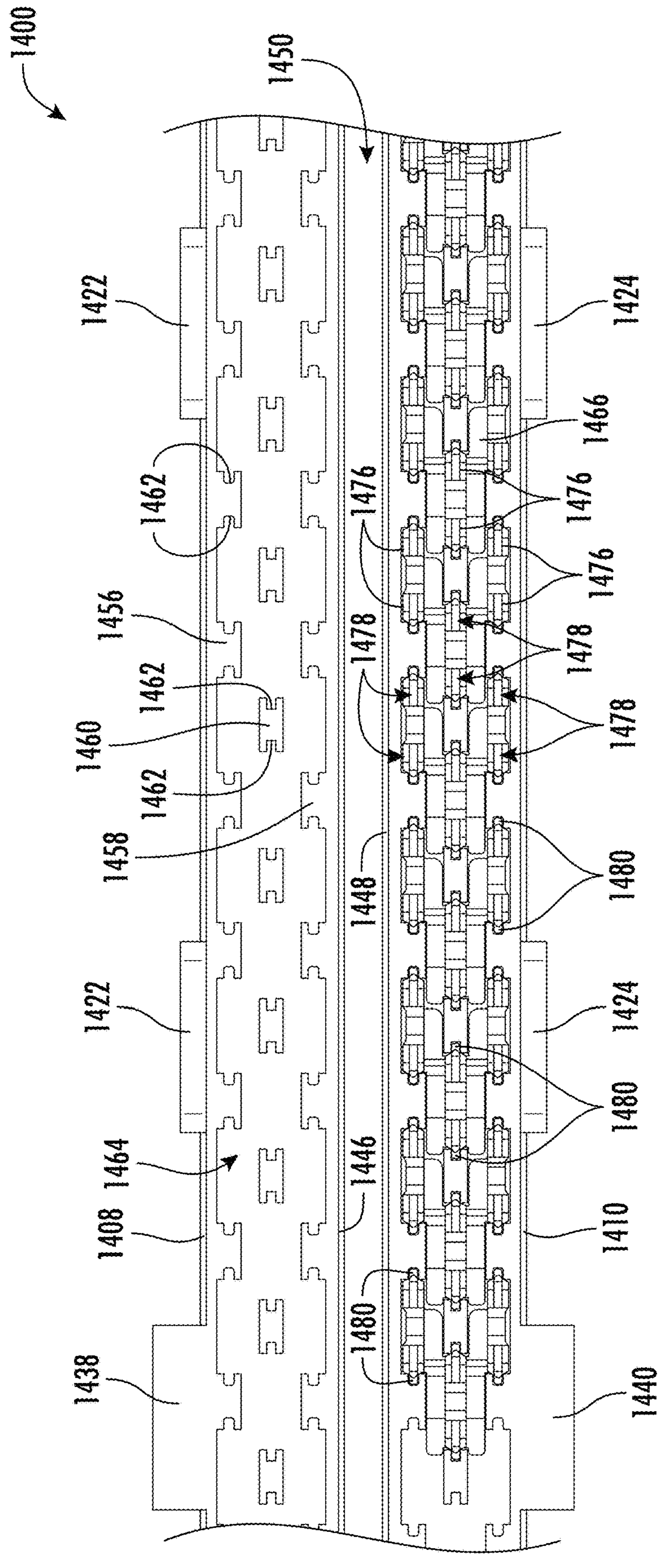
FIG. 17 is a top view of the reload cartridge of FIGS. 14-16.

As shown in FIGS. 15-17, the cartridge 1400 further includes multiple drivers 1466 that are each positioned within a respective driver channel 1464 defined in the cartridge body 1402. Each driver 1466 has a body 1468 with a pair of ramps 1470 that extend proximally from body 1468. An opening 1472 is defined between the ramps 1470. Each of the ramps 1470 includes and angled bottom surface 1474. Multiple pairs of posts 1476 extend upward from the body 1468. Each post 1476 includes a staple saddle 1478 positioned on a top surface of the post 1476, and a pair of tabs 1480 that extend proximally and distally from the post 1476.

As described above, each of the drivers 1466 is positioned within a corresponding driver channel 1464 in the body 1402 of the cartridge 1400. Each driver 1466 may be inserted into the cartridge 1400 via either of the openings 1452, 1454. As shown, when inserted through the opening 1452, 1454, the opening 1472 of each driver 1466 surrounds an inner column 1460 of the cartridge 1400, and the body 1468 of the driver 1466 is surrounded by a pair of inner columns 1456, 1458. The tabs 1480 of the driver 1466 engage corresponding grooves 1462 on the columns 1456, 1458, 1460, which further locates and guides the driver 1466 within the driver channel 1464. One or more surgical staples (not shown) may also be positioned within the driver channel 1464 between the driver 1466 and the deck 1412. A cross-part of each staple may be engaged by a pair of staple saddles 1478 of a corresponding pair of posts 1476, and the prongs of each staple may extend upward toward a staple opening 1442 defined in the deck 1412.

The staple reload cartridge 1400 further includes a sled 1482 that is slideably coupled to the elongated body 1402. The sled 1482 includes a body 1484 with a central fin 1486 that extends upward from the body 1484. The sled 1484 further includes multiple angled outer fins 1488 that extend upward from the body 1484. Each of the angled outer fins 1488 includes an angled upper surface 1490.

The central fin 1486 of the sled 1482 is received in the central slot 1450 defined in the cartridge body 1402. The sled 1482 is initially positioned at the proximal end 1404 of the cartridge body 1402. The sled 1482 may be moved distally toward the distal nose 1406, and the central fin 1486 slides along the central slot 1450. As the sled 1482 moves, each of the angled outer fins 1488 also slides through spaces defined between respective side columns 1456, 1458 and center columns 1460.

As the sled 1482 moves from the proximal end 1404 toward the distal nose 1406, the angled outer fins 1488 sequentially engage the drivers 1466 positioned within the body 1402 of the cartridge 1400. As the angled outer fins 1488 engage each of the drivers 1466, the angled upper surfaces 1490 of the outer fins 1488 bear against the angled bottom surfaces 1474 of the driver 1466, forcing the driver 1466 upward in its respective driver channel 1464. This upward movement of the driver 1466 ejects one or more surgical staples out the corresponding staple openings 1442 defined in the deck 1412.

In the illustrative embodiment shown in FIGS. 14-17, the drivers 1466 are embodied as triple drivers that each contact three surgical staples. That is, each of the drivers 1466 includes three pairs of posts 1476 with three corresponding pairs of staple saddles 1478, and is configured to engage three surgical staples arranged with respect to three staple openings 1442 defined in the deck 1412. This triple driver arrangement may reduce width of the cartridge body 1402, thereby allowing the external grooves 1434, 1436 defined on the outer walls 1408, 1410 to be increased in depth relative to other arrangements. Of course, in other embodiments, different arrangements and/or configurations of drivers 1466 and surgical staples may be used in other embodiments.

The body 1402 of the cartridge 1400 may be formed from a polymeric material using an injection molding process. Accordingly, the body 1402 may include one or more features to facilitate successful injection molding. For example, each of the top rails 1414, 1416 extends the entire length of the body 1402 from the proximal end 1404 to the distal nose 1406, and each of those top rails 1414, 1416 maintains a certain minimum cross-sectional area when viewed along a proximal-distal axis. This minimum cross-sectional area may ensure that injection molding material successfully flows along the length of the body 1402. Similarly, the deck 1412 may maintain a certain minimum thickness over its entire length, which ensures that injection molding material successfully flows along the length of the body 1402, and also flows along the height of the internal columns 1460, from the deck 1412 downward to the openings 1452, 1454.

Figure 18:
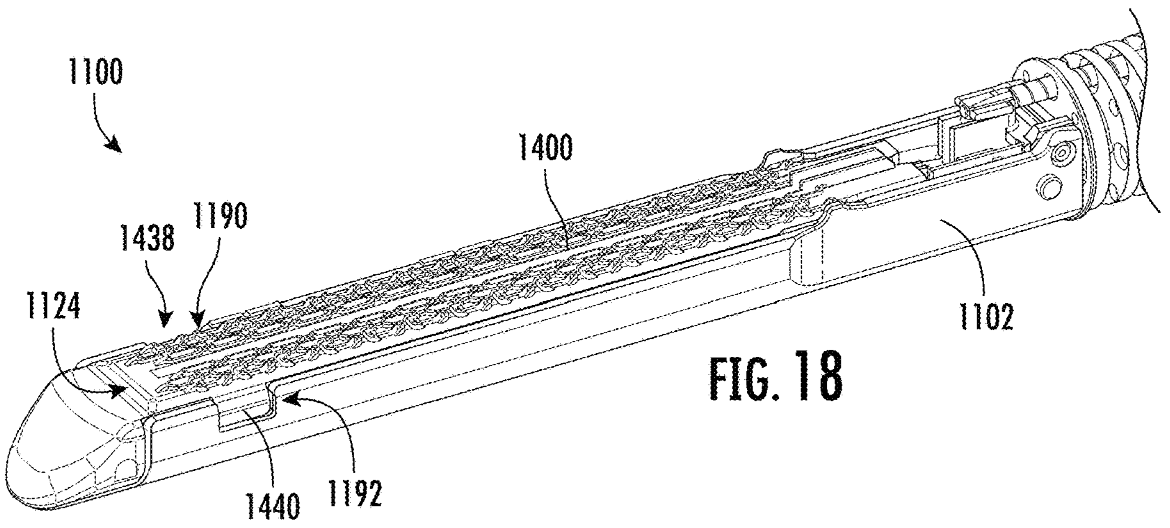
FIG. 18 is a perspective view of a reload cartridge of FIGS. 14-17 loaded in a lower jaw of the end effector of FIGS. 11-13.
Figure 19:
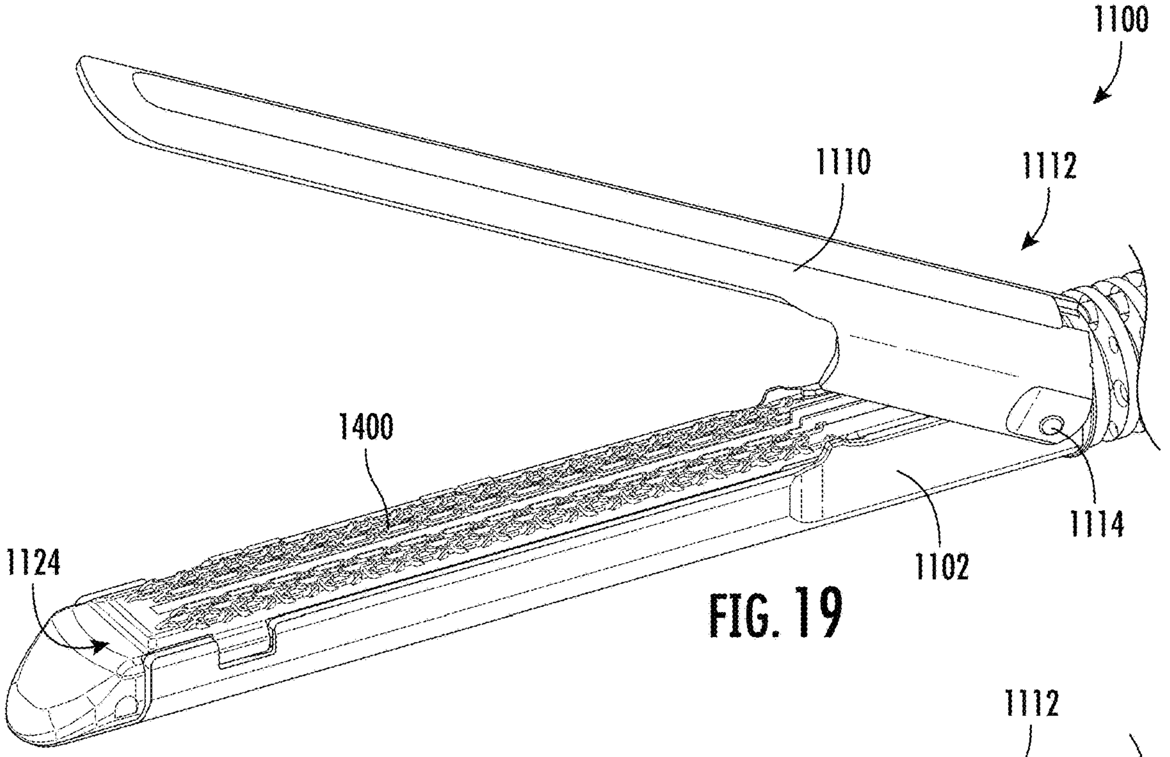
FIG. 19 is a perspective view of a reload cartridge of FIGS. 14-17 loaded in the end effector of FIGS. 11-13 with the end effector in an open state.
Figure 20:
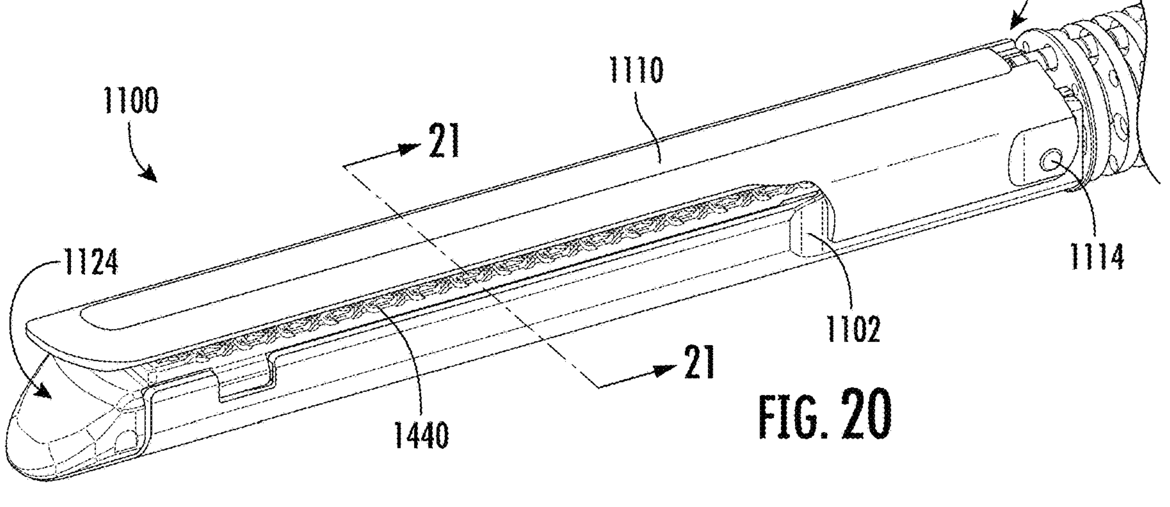
FIG. 20 is a perspective view of a reload cartridge of FIGS. 14-17 loaded in the end effector of FIGS. 11-13 with the end effector in a closed state.

Referring now to FIGS. 18-21, in use a staple reload cartridge 1400 as shown in FIGS. 14-17 may be mounted to an end effector 1100 as shown in FIGS. 11-13 for use in a surgical stapling operation, also called a firing of the instrument 102. As shown in FIGS. 18-19, the cartridge 1400 may be attached to the end effector 1100 by being inserted into the channel 1124 of the cartridge jaw 1102. When inserted into the channel 1124, the tabs 1438, 1440 of the cartridge 1400 are received by the corresponding notches 1190, 1192 defined in the cartridge jaw 1102.

Figure 21:
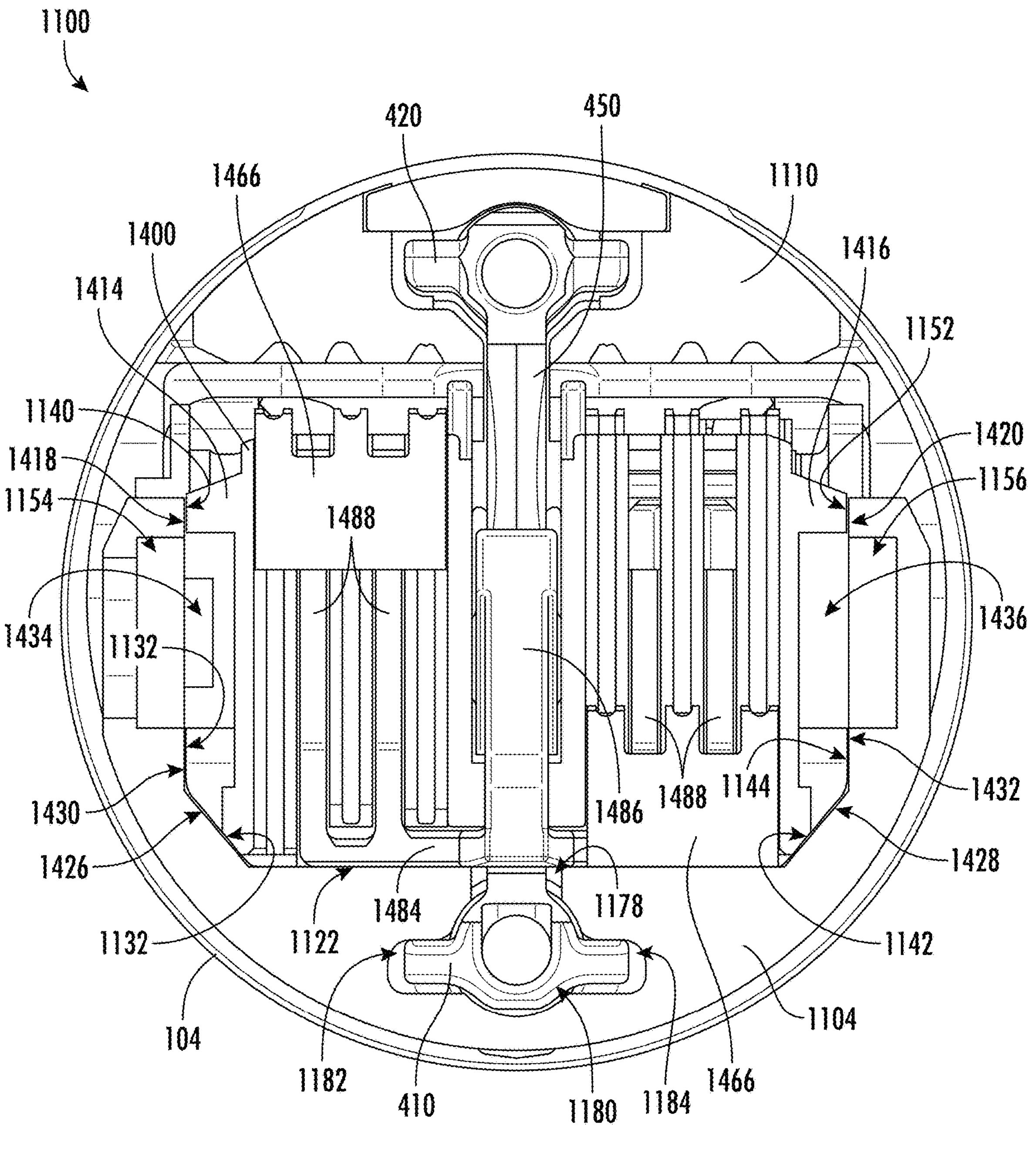
FIG. 21 is a cross-sectional view of the reload cartridge loaded in the end effector with the end effector in the closed state of FIG. 20.

As best shown in FIG. 21, when the cartridge 1400 is loaded in the end effector 1100, the flat outer surfaces 1418, 1420 of the top rails 1114, 1116 of the cartridge 1400 confront and contact respective wall headers 1140, 1152 of the inner surfaces 1126, 1128 of the side walls 1118, 1120. Similarly, the flat outer surfaces 1430, 1432 of the bottom pads 1422, 1424 confront and contact respective wall footers 1132, 1144 of the inner surfaces 1126, 1128. Additionally, the bottom surfaces 1409, 1411 of the side walls 1408, 1410 and/or the side columns 1456 confront and contact the floor 1122 of the end effector 1100. In some embodiments, the bottom chamfers 1426, 1428 of the bottom pads 1422, 1424 confront and contact respective chamfers 1130, 1142 of the inner surfaces 1126, 1128. Additionally or alternatively, in some embodiments, the bottom chamfers 1426, 1428 of the bottom pads 1422, 1424 are spaced apart from and do not contact the respective chamfers 1130, 1142 of the inner surfaces 1126, 1128.

As shown, when the cartridge 1400 is loaded in the end effector 1100, the groove 1154 defined in the side wall 1118 is in communication with the groove 1434 defined in the side wall 1408, and the groove 1156 defined in the side wall 1120 is in communication with the groove 1436 defined in the side wall 1410. Accordingly, the illustrative cartridge 1400 and cartridge jaw 1102 may cooperate to provide free space within the end effector 1100, which may be used for packaging sensors, electronics boards, or other additional features within the end effector 1100.

During a firing operation, the handpiece and/or robotic tool interface causes the drivetrain to move an I-beam 350 of the end effector 1100 from the proximal end 1106 to the distal end 1108. As the I-beam 350 moves distally, the upper beam or wing 420 is received in a slot defined in the anchor 1110 and the lower beam 410 is received in the slot 1178, including the slot bore 1180 and the slot side annexes 1182, 1184. As the I-beam 350 continues to move distally, the upper beam 420 urges the anvil jaw 1110 to swing closed, towards the cartridge jaw 1102. As the anvil jaw 1110 closes, tissue may be clamped between the deck 1412 of the cartridge 1400 and the anvil jaw 1110.

As the I-beam 350 moves distally, it pushes against the sled 1482 of the cartridge 1400 and also causes the sled 1482 to move distally. As described above, as the sled 1482 moves distally, it sequentially forces the drivers 1466 upwards, which causes surgical staples to be ejected upward, out of the staple openings 1442 toward the anvil jaw 1110. As the staples bear against the anvil, they are bent into a shape that clamps the tissue between the deck 1412 and the anvil jaw 1110. Bending the staples into shape and clamping tissues achieves hemostasis. After the sled 1482 has passed the tissue and hemostasis has been achieved, a knife 450 carried by the I-beam 350 cuts (transects) the tissue. This stapling and cutting operation may proceed for the entire length of the deck 1412 of the cartridge 1400.

As shown in FIG. 21, when force is applied to the deck 1412, for example when tissue is clamped between the deck 1410 and the anvil jaw 1110 during a firing of the instrument 102, the force is transferred through the cartridge 1402 down to the floor 1122 of the cartridge jaw 1102. Accordingly, the illustratively cartridge jaw 1102 may maintain structural strength and stability even when including grooves 1154, 1156 that reduce the cross-sectional thickness of the side walls 1118, 1120. Additionally, the illustrative cartridge jaw 1102 may maintain structural strength and stability by maintaining a certain minimum material thickness near the chamfers 1130, 1142. Additionally, the illustrative cartridge jaw 1102 may reduce stress associated with the slot 1178 by including the curved walls 1162, 1164 and/or the curved end walls 1170, 1172, as opposed to a T-slot that includes sharp corners.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

Examples

Example 1 includes a surgical instrument comprising an end effector comprising an elongated jaw that extends to a distal end, wherein the jaw comprises a first side wall, a second side wall, and a floor coupled between the first side wall and the second side wall, wherein the first side wall, the second side wall, and the floor cooperate to define a channel extending to the distal end; wherein the first side wall comprises an inner surface extending upward from the floor, wherein the inner surface comprises a footer, a first ledge extending outwardly from the footer, a groove surface extending upward from the first ledge, a second ledge extending inwardly from the groove surface, and a header extending upward from the second ledge; wherein the first ledge, the groove surface, and the second ledge cooperate to define a groove in the first side wall, wherein the groove is in communication with the channel.

Example 2 includes the subject matter of Example 1, and wherein the end effector further comprises an I-beam comprising a knife that is moveable along the elongated jaw to the distal end; and the surgical instrument further comprises an elongated shaft that extends from a distal end to a proximal end, wherein the distal end of the elongated shaft is coupled to the end effector, and wherein the elongated shaft comprises a drivetrain coupled to the I-beam of the end effector.

Example 3 includes the subject matter of any of Examples 1 and 2, and further comprising a handpiece coupled to the proximal end of the elongated shaft, wherein the handpiece is configured to drive the drivetrain.

Example 4 includes the subject matter of any of Examples 1-3, and further comprising a robotic tool interface coupled to the proximal end of the elongated shaft, wherein the robotic tool interface is configured to drive the drivetrain.

Example 5 includes the subject matter of any of Examples 1-4, and wherein the floor of the elongated jaw further comprises a first slot wall extending downward from the floor and a second slot wall facing the first slot wall and extending downward from the floor in parallel; a first curved slot wall and a second curved slot wall extending outward from the first slot wall and the second slot wall, respectively, in opposing directions; and a slot floor connecting the first curved slot wall and the second curved slot wall; and the first slot wall, the second slot wall, the first curved slot wall, the second curved slot wall, and the slot floor cooperate to define an elongated slot that extends to the distal end, wherein the slot is in communication with the channel.

Example 6 includes the subject matter of a Example 5, and wherein the first curved slot wall further comprises a first inner cutout wall that extends outward to a first curved end wall; the second curved slot wall further comprises a second inner cutout wall that extends outward, in an opposing direction to the first inner cutout wall, to a second curved end wall; wherein the first inner cutout wall and the first curved end wall cooperate to define a first slot side annex, and the second inner cutout wall and the second curved end wall cooperate to define of a second slot side annex.

Example 7 includes the subject matter of any of Examples 5 and 6, and wherein the end effector further comprises an I-beam comprising a knife and a lower beam, wherein the lower beam is received in the slot.

Example 8 includes the subject matter of any of Examples 5-7, and further comprising an elongated shaft that extends from a distal end to a proximal end, wherein the distal end is coupled to the end effector, and wherein the elongated shaft comprises a drivetrain coupled to the I-beam.

Example 9 includes the subject matter of Example 8, and further comprising a handpiece coupled to the proximal end of the elongated shaft, wherein the handpiece is configured to drive the drivetrain.

Example 10 includes the subject matter of Example 8, and further comprising a robotic tool interface coupled to the proximal end of the elongated shaft, wherein the handpiece is configured to drive the drivetrain.

Example 11 includes the subject matter of any of Examples 1-10, wherein the jaw extends from a hinge to the distal end, and wherein the end effector further comprises an elongated anvil extending from a proximal end to a distal end, wherein the proximal end is hingedly coupled to the hinge of the jaw, wherein the anvil is rotatable about the hinge from an open position in which the distal end of the anvil is spaced apart from the distal end of the jaw to a closed position in which the distal end of the anvil is close to the distal end of the jaw.

Example 12 includes the subject matter of any of Examples 1-11, and further comprising an elongated staple cartridge positioned in the channel of the jaw, wherein the staple cartridge comprises an elongated body extending from a proximal end to a distal nose; wherein the elongated body comprises: a first side wall extending from the proximal end to the distal nose, wherein the first side wall comprises a top rail extending outward from a top edge of the first side wall and extending from the proximal end to the distal nose, and wherein the first side wall comprises a first bottom pad extending outward from a bottom edge of the first side wall, and wherein the first side wall, the top rail, and the first bottom pad cooperate to define a side groove; wherein an outer surface of the top rail of the staple cartridge engages the header of the first side wall, an outer surface of the first bottom pad engages the footer of the first side wall, and a bottom surface of the first side wall engages the floor of the jaw; wherein the side groove defined in the staple cartridge is in communication with the groove defined in the first side wall.

Example 13 includes the subject matter of Example 12, and wherein the first bottom pad is positioned at an intermediate position between the proximal end and the distal nose.

Example 14 includes the subject matter of any of Examples 12 and 13, and further comprising a second bottom pad extending outward from the bottom edge of the first side wall, wherein the second bottom pad is positioned at a second intermediate position between the proximal end and the distal nose.

Example 15 includes the subject matter of Example 12, and wherein the first bottom pad extends from the proximal end to the distal nose.

Example 16 includes the subject matter of any of Examples 1-15, and wherein the elongated body further comprises a deck extending from the proximal end to the distal nose, wherein the deck is coupled to the first side wall at the top rail, and a first inner wall extending downward from the deck, and extending parallel to the first side wall from the proximal end to a first position proximal of the distal nose; wherein a central slot is defined through the deck by the first inner wall from the proximal end to the first position; wherein a plurality of staple openings are defined in the deck; and wherein an elongated bottom opening opposite the plurality of staple openings is defined between the first side wall and the first inner wall.

Example 17 includes the subject matter of Example 16, and further comprising a first side column coupled to the first side wall and extending from the deck to the bottom opening, wherein a bottom surface of the first side column engages the floor of the jaw; a second side column coupled to the first inner wall and extending from the deck to the bottom opening; and a first inner column extending from the deck to the bottom opening; wherein the first side column, the second side column, and the first inner column cooperate to define a first driver channel from the bottom opening to one or more staple openings of the plurality of staple openings.

Example 18 includes the subject matter of Example 17, and further comprising a first surgical staple positioned in the first driver channel; and a first driver positioned in the first driver channel, the first driver having a top saddle configured to engage the first surgical staple, wherein the first surgical staple is positioned between the first driver and the deck; wherein when the first driver is moved within the first driver channel from a first position that is closer to the bottom opening to a second position that is closer to the one or more staple openings, the first driver ejects the first surgical staple out of the one or more staple openings.

Example 19 includes the subject matter of Example 18, and further comprising a second surgical staple and a third surgical staple positioned in the first driver channel; wherein the first driver further comprises a second top saddle configured to engage the second surgical staple and a third top saddle configured to engage the third surgical staple; wherein when the first driver is moved within the first driver channel from the first position to the second position, the first driver ejects the second surgical staple and the third surgical staple out of the one or more staple openings.

Example 20 includes the subject matter of any of Examples 1-19, and further comprising a sled coupled to the elongated body, the sled having a central fin that extends upward into the central slot and a first angled fin that extends upward through the bottom opening; wherein the sled is moveable from a proximal position to a distal position; and wherein when the sled is moved from the proximal position to the distal position, the first angled fin engages an angled bottom surface of the first driver and causes the first driver to move from the first position to the second position.

Example 21 includes a staple cartridge for a surgical instrument, the cartridge comprising an elongated body extending from a proximal end to a distal nose; wherein the elongated body comprises: a first side wall extending from the proximal end to the distal nose, wherein the first side wall comprises a top rail extending outward from a top edge of the first side wall and extending from the proximal end to the distal nose, and wherein the first side wall comprises a first bottom pad extending outward from a bottom edge of the first side wall, and wherein the first side wall, the top rail, and the first bottom pad cooperate to define a side groove.

Example 22 includes the subject matter of Example 21, and wherein the top rail comprises a flat outer surface, wherein the bottom pad comprises a flat outer surface, and wherein the first side wall comprises a bottom surface.

Example 23 includes the subject matter of any of Examples 21 and 22, and wherein the first bottom pad is positioned at an intermediate position between the proximal end and the distal nose.

Example 24 includes the subject matter of any of Examples 21-23, and further comprising a second bottom pad extending outward from the bottom edge of the first side wall, wherein the second bottom pad is positioned at a second intermediate position between the proximal end and the distal nose.

Example 25 includes the subject matter of any of Examples 21-23, and wherein the first bottom pad extends from the proximal end to the distal nose.

Example 26 includes the subject matter of any of Examples 21-25, and wherein the elongated body further comprises a deck extending from the proximal end to the distal nose, wherein the deck is coupled to the first side wall at the top rail, and a first inner wall extending downward from the deck, and extending parallel to the first side wall from the proximal end to a first position proximal of the distal nose; wherein a central slot is defined through the deck by the first inner wall from the proximal end to the first position; wherein a plurality of staple openings are defined in the deck; and wherein an elongated bottom opening opposite the plurality of staple openings is defined between the first side wall and the first inner wall.

Example 27 includes the subject matter of Example 26, and further comprising a first side column coupled to the first side wall and extending from the deck to the bottom opening; a second side column coupled to the first inner wall and extending from the deck to the bottom opening; and a first inner column extending from the deck to the bottom opening; wherein the first side column, the second side column, and the first inner column cooperate to define a first driver channel from the bottom opening to one or more staple openings of the plurality of staple openings.

Example 28 includes the subject matter of Example 27, and further comprising a first surgical staple positioned in the first driver channel; and a first driver positioned in the first driver channel, the first driver having a top saddle configured to engage the first surgical staple, wherein the first surgical staple is positioned between the first driver and the deck; wherein when the first driver is moved within the first driver channel from a first position that is closer to the bottom opening to a second position that is closer to the one or more staple openings, the first driver ejects the first surgical staple out of the one or more staple openings.

Example 29 includes the subject matter of Example 28, and further comprising a second surgical staple and a third surgical staple positioned in the first driver channel; wherein the first driver further comprises a second top saddle configured to engage the second surgical staple and a third top saddle configured to engage the third surgical staple; wherein when the first driver is moved within the first driver channel from the first position to the second position, the first driver ejects the second surgical staple and the third surgical staple out of the one or more staple openings.

Example 30 includes the subject matter of any of Examples 21-29, and further comprising a sled coupled to the elongated body, the sled having a central fin that extends upward into the central slot and a first angled fin that extends upward through the bottom opening; wherein the sled is moveable from a proximal position to a distal position; and wherein when the sled is moved from the proximal position to the distal position, the first angled fin engages an angled bottom surface of the first driver and causes the first driver to move from the first position to the second position.

The invention claimed is:

1. A surgical instrument comprising:

an end effector comprising an elongated jaw that extends to a distal end, wherein the jaw comprises a first side wall, a second side wall, and a floor coupled between the first side wall and the second side wall, wherein the first side wall, the second side wall, and the floor cooperate to define a channel extending to the distal end;

wherein the first side wall comprises an inner surface extending upward from the floor, wherein the inner surface comprises a footer, a first ledge extending outwardly from the footer, a groove surface extending upward from the first ledge, a second ledge extending inwardly from the groove surface, and a header extending upward from the second ledge;

wherein the first ledge, the groove surface, and the second ledge cooperate to define a groove in the first side wall, wherein the groove is in communication with the channel.

2. The surgical instrument of claim 1, wherein:

the end effector further comprises an I-beam comprising a knife that is moveable along the elongated jaw to the distal end;

and the surgical instrument further comprises an elongated shaft that extends from a distal end to a proximal end, wherein the distal end of the elongated shaft is coupled to the end effector, and wherein the elongated shaft comprises a drivetrain coupled to the I-beam of the end effector.

3. The surgical instrument of claim 2, further comprising a handpiece coupled to the proximal end of the elongated shaft, wherein the handpiece is configured to drive the drivetrain.

4. The surgical instrument of claim 2, further comprising a robotic tool interface coupled to the proximal end of the elongated shaft, wherein the robotic tool interface is configured to drive the drivetrain.

5. The surgical instrument of claim 1, wherein:

the floor of the elongated jaw further comprises a first slot wall extending downward from the floor and a second slot wall facing the first slot wall and extending downward from the floor in parallel; a first curved slot wall and a second curved slot wall extending outward from the first slot wall and the second slot wall, respectively, in opposing directions; and a slot floor connecting the first curved slot wall and the second curved slot wall; and the first slot wall, the second slot wall, the first curved slot wall, the second curved slot wall, and the slot floor cooperate to define an elongated slot that extends to the distal end, wherein the slot is in communication with the channel.

6. The surgical instrument of claim 5, wherein:

the first curved slot wall further comprises a first inner cutout wall that extends outward to a first curved end wall; and the second curved slot wall further comprises a second inner cutout wall that extends outward, in an opposing direction to the first inner cutout wall, to a second curved end wall;

wherein the first inner cutout wall and the first curved end wall cooperate to define a first slot side annex, and the second inner cutout wall and the second curved end wall cooperate to define of a second slot side annex.

7. The surgical instrument of claim 5, wherein the end effector further comprises an I-beam comprising a knife and a lower beam, wherein the lower beam is received in the slot.

8. The surgical instrument of claim 5, further comprising an elongated shaft that extends from a distal end to a proximal end, wherein the distal end is coupled to the end effector, and wherein the elongated shaft comprises a drivetrain coupled to the I-beam.

9. The surgical instrument of claim 8, further comprising a handpiece coupled to the proximal end of the elongated shaft, wherein the handpiece is configured to drive the drivetrain.

10. The surgical instrument of claim 8, further comprising a robotic tool interface coupled to the proximal end of the elongated shaft, wherein the handpiece is configured to drive the drivetrain.

11. The surgical instrument of claim 1, wherein the jaw extends from a hinge to the distal end, and wherein the end effector further comprises an elongated anvil extending from a proximal end to a distal end, wherein the proximal end is hingedly coupled to the hinge of the jaw, wherein the anvil is rotatable about the hinge from an open position in which the distal end of the anvil is spaced apart from the distal end of the jaw to a closed position in which the distal end of the anvil is close to the distal end of the jaw.

12. The surgical instrument of claim 1, further comprising an elongated staple cartridge positioned in the channel of the jaw, wherein the staple cartridge comprises:

an elongated body extending from a proximal end to a distal nose; wherein the elongated body comprises:

a first side wall extending from the proximal end to the distal nose, wherein the first side wall comprises a top rail extending outward from a top edge of the first side wall and extending from the proximal end to the distal nose, and wherein the first side wall comprises a first bottom pad extending outward from a bottom edge of the first side wall, and wherein the first side wall, the top rail, and the first bottom pad cooperate to define a side groove;

wherein an outer surface of the top rail of the staple cartridge engages the header of the first side wall, an outer surface of the first bottom pad engages the footer of the first side wall, and a bottom surface of the first side wall engages the floor of the jaw;

wherein the side groove defined in the staple cartridge is in communication with the groove defined in the first side wall.

13. The surgical instrument of claim 12, wherein the first bottom pad is positioned at an intermediate position between the proximal end and the distal nose.

14. The surgical instrument of claim 13, further comprising a second bottom pad extending outward from the bottom edge of the first side wall, wherein the second bottom pad is positioned at a second intermediate position between the proximal end and the distal nose.

15. The surgical instrument of claim 12, wherein the first bottom pad extends from the proximal end to the distal nose.

16. The surgical instrument of claim 1, wherein the elongated body further comprises:

a deck extending from the proximal end to the distal nose, wherein the deck is coupled to the first side wall at the top rail; and a first inner wall extending downward from the deck, and extending parallel to the first side wall from the proximal end to a first position proximal of the distal nose;

wherein a central slot is defined through the deck by the first inner wall from the proximal end to the first position;

wherein a plurality of staple openings are defined in the deck; and wherein an elongated bottom opening opposite the plurality of staple openings is defined between the first side wall and the first inner wall.

17. The surgical instrument of claim 16, further comprising a first side column coupled to the first side wall and extending from the deck to the bottom opening, wherein a bottom surface of the first side column engages the floor of the jaw;

a second side column coupled to the first inner wall and extending from the deck to the bottom opening; and a first inner column extending from the deck to the bottom opening;

wherein the first side column, the second side column, and the first inner column cooperate to define a first driver channel from the bottom opening to one or more staple openings of the plurality of staple openings.

18. The surgical instrument of claim 17, further comprising:

a first surgical staple positioned in the first driver channel; and a first driver positioned in the first driver channel, the first driver having a top saddle configured to engage the first surgical staple, wherein the first surgical staple is positioned between the first driver and the deck;

wherein when the first driver is moved within the first driver channel from a first position that is closer to the bottom opening to a second position that is closer to the one or more staple openings, the first driver ejects the first surgical staple out of the one or more staple openings.

19. The surgical instrument of claim 18, further comprising:

a second surgical staple and a third surgical staple positioned in the first driver channel;

wherein the first driver further comprises a second top saddle configured to engage the second surgical staple and a third top saddle configured to engage the third surgical staple;

wherein when the first driver is moved within the first driver channel from the first position to the second position, the first driver ejects the second surgical staple and the third surgical staple out of the one or more staple openings.

20. The surgical instrument of claim 1, further comprising:

a sled coupled to the elongated body, the sled having a central fin that extends upward into the central slot and a first angled fin that extends upward through the bottom opening;

wherein the sled is moveable from a proximal position to a distal position; and wherein when the sled is moved from the proximal position to the distal position, the first angled fin engages an angled bottom surface of the first driver and causes the first driver to move from the first position to the second position.

* * * * *